United States Patent [19]
Beierlorzer

[11] Patent Number: 5,871,432
[45] Date of Patent: Feb. 16, 1999

[54] METHOD AND APPARATUS FOR MAKING AN IMPROVED RESILIENT PACKING PRODUCT

[75] Inventor: Edwin P. Beierlorzer, Bellevue, Wash.

[73] Assignee: Ranpak Corp., Concord Township, Ohio

[21] Appl. No.: 153,491

[22] Filed: Nov. 17, 1993

Related U.S. Application Data

[63] Continuation of Ser. No. 861,225, Mar. 31, 1992, abandoned.

[51] Int. Cl.⁶ .................. B31F 1/00; B31F 5/02; B31F 1/12; B30B 15/08
[52] U.S. Cl. ............ 493/352; 493/463; 493/464; 493/967
[58] Field of Search .................. 493/328, 352, 493/357, 362, 365, 407, 463, 464, 967

[56] References Cited

U.S. PATENT DOCUMENTS

| | | |
|---|---|---|
| 1,680,203 | 8/1928 | Cannard .................. 493/967 |
| 1,985,676 | 12/1934 | Hand . |
| 2,045,498 | 6/1936 | Stevenson .................. 28/1 |
| 2,271,180 | 1/1942 | Brugger . |
| 2,537,026 | 1/1951 | Brugger . |
| 2,621,567 | 12/1952 | Lee .................. 493/967 |
| 2,668,573 | 2/1954 | Larsson .................. 154/30 |
| 2,686,466 | 8/1954 | Lee .................. 100/97 |
| 2,697,887 | 12/1954 | Doyle et al. .................. 428/152 |
| 2,770,302 | 11/1956 | Lee .................. 164/60 |
| 2,786,399 | 3/1957 | Mason et al. .................. 493/967 |
| 2,825,556 | 3/1958 | Rowe . |
| 2,865,080 | 12/1958 | Hentschel . |
| 2,924,154 | 2/1960 | Russell et al. . |
| 2,968,857 | 1/1961 | Swerdloff et al. . |
| 2,984,399 | 5/1961 | Gaulke . |
| 3,126,095 | 3/1964 | Caines et al. . |
| 3,150,576 | 9/1964 | Gewiss . |
| 3,217,988 | 11/1965 | Lightfoot et al. . |
| 3,235,442 | 2/1966 | Stump . |
| 3,398,223 | 8/1968 | Schatz et al. . |
| 3,501,565 | 3/1970 | Kalwaites et al. . |
| 3,509,797 | 5/1970 | Johnson . |
| 3,514,096 | 5/1970 | Muller . |
| 3,567,119 | 3/1971 | Wilbert . |
| 3,613,522 | 10/1971 | Johnson . |
| 3,650,877 | 3/1972 | Johnson . |
| 3,754,498 | 8/1973 | Gil . |
| 3,859,695 | 1/1975 | Erickson . |
| 3,905,057 | 9/1975 | Willis et al. . |
| 4,012,932 | 3/1977 | Gewiss . |
| 4,075,746 | 2/1978 | Roberts . |
| 4,085,662 | 4/1978 | Ottaviano . |
| 4,091,766 | 5/1978 | Colliard . |
| 4,132,155 | 1/1979 | Hicks et al. . |
| 4,201,128 | 5/1980 | Whitehead et al. . |
| 4,247,289 | 1/1981 | McCabe . |
| 4,313,899 | 2/1982 | Hein . |
| 4,410,315 | 10/1983 | Frye . |
| 4,551,126 | 11/1985 | Johnson et al. .................. 493/453 |
| 4,597,748 | 7/1986 | Wolf . |
| 4,619,862 | 10/1986 | Sokolowski et al. . |
| 4,622,028 | 11/1986 | Bunch, Jr. . |

(List continued on next page.)

FOREIGN PATENT DOCUMENTS

| | | |
|---|---|---|
| 666 225 | 8/1948 | United Kingdom . |
| 771877 | 3/1957 | United Kingdom . |
| WO 91/06694 | 5/1991 | WIPO . |

*Primary Examiner*—Jack W. Lavinder
*Attorney, Agent, or Firm*—Renner, Otto, Boisselle & Sklar, P.L.L.

[57] ABSTRACT

The present invention relates of a method and apparatus for making an improved resilient packing material by forming, resiliently folding and crimping shredded strips of moistened paper material into an improved interlocking, bulk, packaging material. The method and apparatus includes a wetting or dampening system which can be selectively varied to regulate the moisture content of moistened paper material.

17 Claims, 11 Drawing Sheets

U.S. PATENT DOCUMENTS

| | | |
|---|---|---|
| 4,650,456 | 3/1987 | Armington . |
| 4,699,609 | 10/1987 | Komaransky et al. . |
| 4,700,939 | 10/1987 | Hathaway . |
| 4,717,135 | 1/1988 | Hathaway . |
| 4,718,654 | 1/1988 | Ehlers . |
| 4,741,944 | 5/1988 | Jackson et al. . |
| 4,806,410 | 2/1989 | Armington et al. . |
| 4,808,466 | 2/1989 | Kotani et al. . |
| 4,813,996 | 3/1989 | Gardner et al. . |
| 4,816,320 | 3/1989 | St. Cyr . |
| 4,868,037 | 9/1989 | McCullough, Jr. et al. . |
| 4,889,755 | 12/1989 | Charbonneau . |
| 4,923,745 | 5/1990 | Wolfert et al. . |
| 4,957,063 | 9/1990 | Heitfeld et al. . |
| 5,016,568 | 5/1991 | Stanislowski et al. . |
| 5,018,482 | 5/1991 | Stanislowski et al. . |
| 5,088,972 | 2/1992 | Parker . |
| 5,097,799 | 3/1992 | Heitfeld et al. . |
| 5,100,600 | 3/1992 | Keller et al. . |
| 5,102,715 | 4/1992 | Zetterquist . |
| 5,134,013 | 7/1992 | Parker . |
| 5,173,352 | 12/1992 | Parker . |
| 5,181,614 | 1/1993 | Watts . |

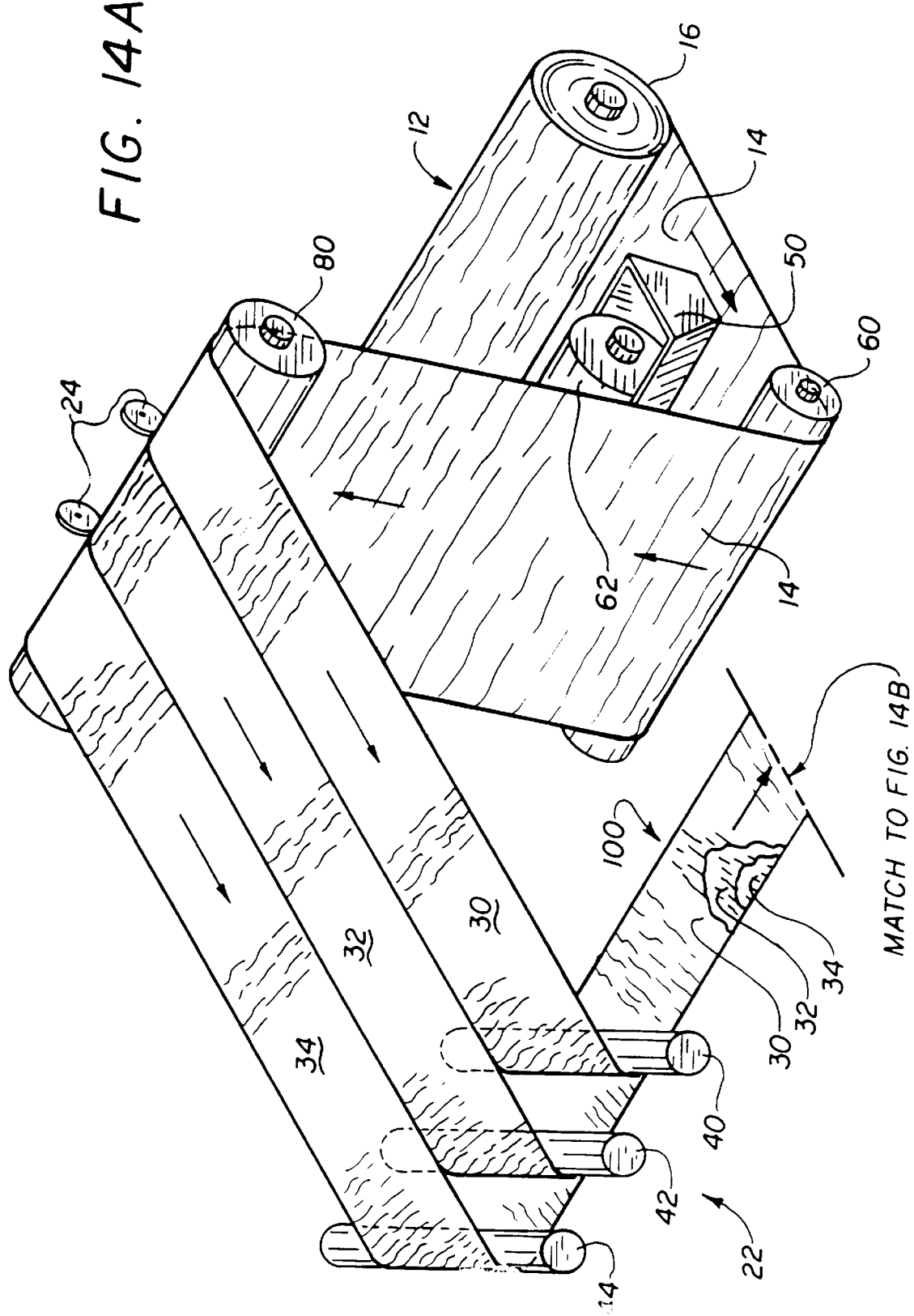

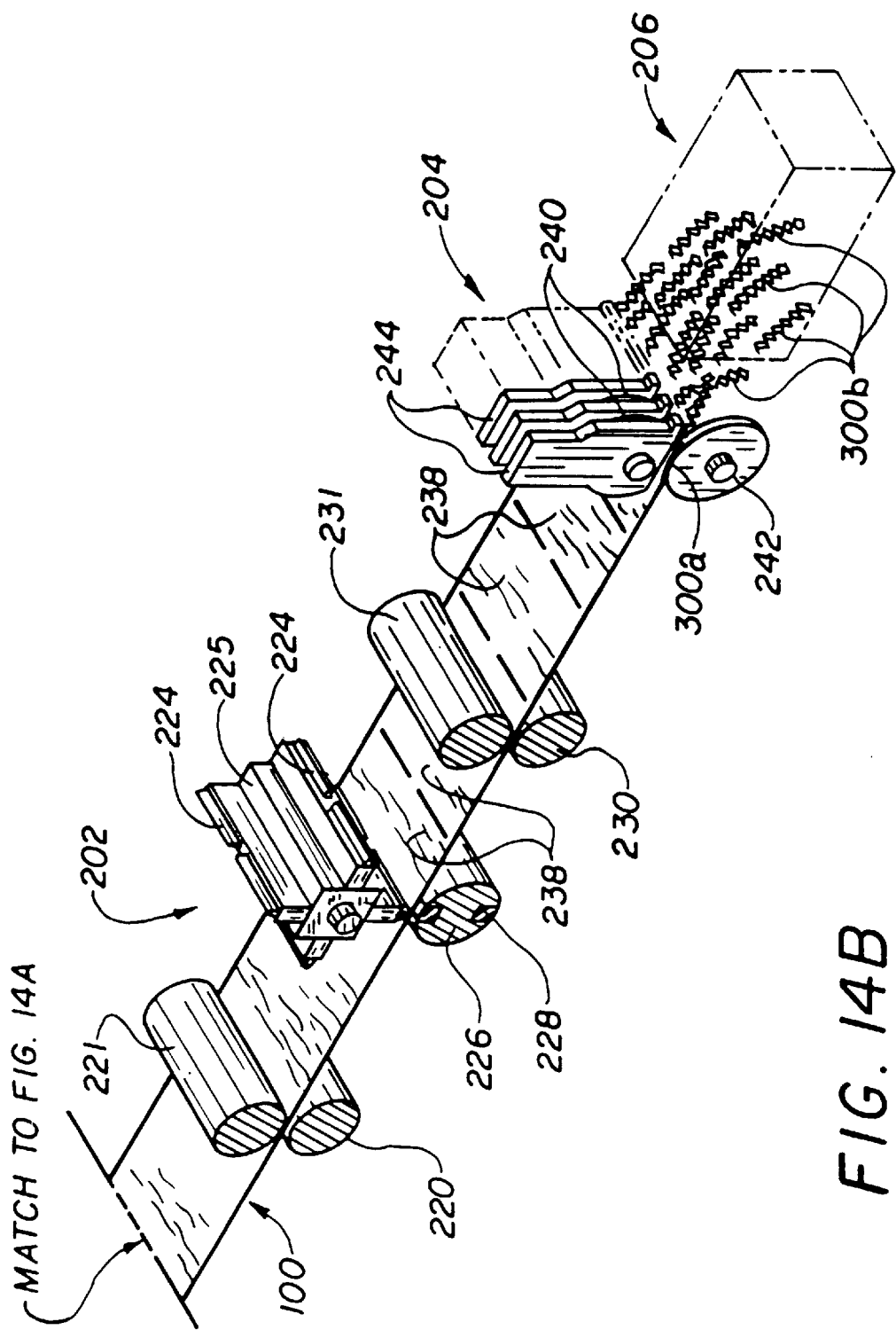

METHOD AND APPARATUS FOR MAKING AN IMPROVED RESILIENT PACKING PRODUCT

This is a continuation of application(s) Ser. No. 07/861,225 filed on Mar. 31, 1992 abandoned.

BACKGROUND OF THE INVENTION

1. Field of the Invention

The present invention relates of a method and apparatus for making an improved resilient packing material. More particularly, this invention relates to such apparatus and methods for forming, resiliently folding and crimping shredded strips of moistened sheet material into an improved interlocking, bulk, packaging material.

2. Description of the Prior Art

Styrofoam pellets or peanuts are commonly used within the wholesale and retail industries as bulk packaging material. The peanuts are used to position a product away from the interior sides of a container and fill the empty space located therebetween. The peanuts are intended to protect the packaged product against the impact or a blow or other mistreatment.

Dispensing styrofoam peanuts does not require a great degree of sophistication. The peanuts are simply gravity fed from large retainer bins into the empty spaces within a packaging container.

Use of styrofoam peanuts, however, has many drawbacks. For example, if styrofoam peanuts are used to protect a heavy object placed within a container, and such package is jostled and shaken, the object tends to gravitate toward the bottom of the container and the peanuts float upward. Eventually the object can come to rest against the base or side of the container and damage to the object may occur. The light weight of the styrofoam peanuts also allows them to be easily blown by the wind and scattered.

It is of particular concern that the styrofoam peanuts are extremely difficult to dispose of and destroy after use. In fact, because of the extensive use of this nonbiodegradable product, which emits toxic gases if burned, styrofoam peanuts present a major threat to the environment and are being banned from an increasing number of communities.

Styrofoam peanuts are also dangerous to children and to wildlife who often mistake them as food and consequently ingest them. Styrofoam peanuts are not digestible and cause a major source of tracheal blockage in children.

Other packaging filler materials, such as shredded paper, have also been used. Shredded paper, however, usually lays flat within the container and a very large amount of paper is required to provide the bulk needed to fill the voids and to protect the contained object. To provide such a large amount of shredded paper is often cost prohibitive and, following its use, such voluminous amounts of paper must be disposed. In addition, the shock absorbency of flat shredded paper is minimal.

U.S. Pat. No. 5,088,972, by Johnny M. Parker, entitled FOLDING AND CRIMPING APPARATUS, which issued on Nov. 18, 1992, discloses apparatus and method for forming a packing material which eliminates some of the undesired features of the products discussed hereinabove. The apparatus and method is for folding and crimping shredded strips of sheet material into preselected lengths of interlocking, decorative material and/or bulk packing material. The apparatus generally includes an attachment for a commercial paper shredding device for shredded sheet material therein. The apparatus comprises a movable barrier against which the shredded strips of sheet material are impelled upon being expelled from cutting blades of the shredding device. The movable barrier causes the strips to become controllably jammed within a confined area between the barrier and the cutting blades. Further insertion of additional strips into the confined area causes the strips to become compacted, folded, and crimped against a remaining dam of jammed sheet material located within the confined area. This causes the strips to fold and press against themselves and form lengths of thin sheet material having an accordian shape configuration.

U.S. application Ser. No. 538,181, by Johnny M. Parker, entitled RESILIENT PACKING PRODUCT AND METHOD AND APPARATUS FOR MAKING THE SAME, was filed on Jun. 14, 1990, to disclose an improved method and apparatus for forming such a resilient packing product and further details regarding the desired characteristics and features of such resilient packing product. The method of producing the packing product as disclosed therein includes the steps of feeding at least one sheet of material in a first direction; cutting the sheet of material into a plurality of strips; the cutting being performed by rotating two sets of alternating, overlapping cutting discs; the feeding of the sheet of material being between the two sets of cutting discs; advancing each of the strips by the rotating of at least an outer surface of a corresponding one of the cutting discs as the outer surface moves in the first direction; restricting each strip from continued advancing in the first direction; and sequentially folding each of the strip means by the restricting and opposition to the advancing. There is included apparatus and means for producing the packing product with the resulting packing product including a plurality of narrow, elongated strips of material which has a natural resilience. Each of the strips includes a plurality of transverse folds against the natural resilience to form a longitudinally compressed strip element.

While the resilient packing product formed by the method and machines as disclosed in U.S. Pat. No. 5,088,972 and in U.S. application Ser. No. 538,181 have produced a satisfactory resilient packing product, some of the characteristics thereof which are highly desirable have not always been capable of being simply and readily reproduced. In one major embodiment of the invention disclosed therein, Kraft paper is utilized in roll form to continuously produce the desired longitudinally compressed strip means. Each longitudinally compressed strip means includes a plurality of transverse folds with generally longitudinal planar sections therebetween. Repeated, controlled formation of such strip means requires the folds to be formed in opposition to the natural resilience of the paper. As clearly disclosed in U.S. application Ser. No. 538,181, the initial formation of these folds results in the longitudinal planar sections at either side of the fold being generally brought into full contact. After each strip means is allowed to "relax", the angle of each fold between the longitudinal planar sections at opposite sides of the fold tends to enlarge under the natural biasing of the paper material from which the strip means are formed.

Although it is desirable for there to be some relaxation of the angle at the folds between the longitudinal planar sections, the general amount of this angle at each fold and its subsequent ability to be maintained in a generally acute form does affect the quality of the packing product. In other words, the preferred packing product does not simply include the formation of such folds which could eventually relax to form an obtuse angle between the adjacent longitudinal planar sections at either side of the folds. Such a "relaxed" longitudinally compressed strip means would not have some of the desired characteristics of resilience and side lateral support which is highly desired.

Consequently, while the inventions disclosed in U.S. Pat. No. 5,088,972 and U.S. application Ser. No. 538,181 do produce a desired packing product having general characteristics for resilience as taught therein, any method or apparatus which could be employed to insure or improve the preferred quality of the packing product would be desirable. In this regard, U.S. Pat. No. 5,088,972 and U.S. application Ser. No. 538,181 disclose means for varying the resistance to the discharge of the plurality of strip means which are formed by the cutting means. This variation in the resistance in the confined area following the array of cutting discs does vary the force created on each of the longitudinally compressed strip means.

However, it has been found that the general humidity in the manufacturing facility during the production of such packing material tends to affect the quality of the resilient packing product. If there was a relatively low humidity, the amount of resistance created at the discharge of the cutting means would be at a relatively high level while if the facility had a higher humidity, the amount of resistance created would need to be adjusted to a different lower level in order to try to reproduce the same desired characteristics of the longitudinally compressed strip means of the preferred resilient packing product.

U.S. Pat. Nos. 1,680,203; 2,668,573; 2,679,887; 2,786,399; and 3,150,576 disclose method and apparatus for generally crinkling, crumpling or folding sheet material.

U.S. Pat. No. 1,680,203 relates to crepe as a product and to the method and apparatus for making the same. The method and apparatus is for making the product whether the web is dry, wet or, preferably, moistened. There is included means for feeding the web but for affecting the crowding of different portions thereof with the relative different pressures and at different angles whereby there is produced in the web crinkles, crepes or waves extending in relatively different directions and being of relative different but predetermined densities.

U.S. Pat. No. 2,668,573 is for corrugating paper. The invention disclosed therein employed material dampened to a suitable extent., which was passed by feed rollers into a channel for the production of the corrugated form. The channel included two parallel surfaces which were spaced corresponding to the heights of the finished waves. The channel includes rollers or plates which have been warmed or heated to a suitable extent. In this way, the ridges of the waves or the tops of the corrugations which got along the warm surfaces would first be dried up or, as it were, made permanent. The corrugations brought about in this way were very close together with adjacent tops or ridges touching or nearly touching one another.

U.S. Pat. No. 2,679,887 discloses a method of crinkling or crimping of paper previously coated with polyethylene resin or laminated with polyethylene film. The web passes beneath the drum which extends into a tank containing water which is heated to a suitable temperature to cause the polyethylene as it passes through the tank to be conditioned so as to be soft and pliable without becoming materially tacky or losing its shape or flowing. In addition to conditioning the polyethylene, the passage of the composite web through the tank serves to condition the paper in the usual manner for the subsequent crinkling and corrugating operation, the time the material is subjected to the bath being such as to affect such conditioning of the paper.

U.S. Pat. No. 2,786,399 is directed to the formation of bodies of crumpled sheet material of the type particularly adapted for the use as engine oil filter elements. During the operation, elongated strips or sheets of newsprint paper are progressively and continuously advanced after the two strips of paper pass upwardly between rollers, the paper is passed beneath a nozzle through which a spray of air-drying resinent plastic material mixed with water is directed downwardly to the surface of the paper. As the paper passes through a crumpling mechanism, the resinus plastic is allowed to dry at room temperature.

U.S. Pat. No. 3,150,576 discloses a process and apparatus for forming transversely corrugations of all forms in sheet or bands of malleable material. With the preferred malleable material being paper, the paper is advanced for movement between herringbone forms by an inlet nozzle which is connected to a supply of suitable hot fluid under pressure, such as steam, to precondition the material prior to the final formation thereof.

U.S. Pat. Nos. 1,680,203; 2,679,887; 2,768,399; and 3,150,567 disclose the step of adding steam, water or some other wetting agent to material in sheet form prior to the manipulation, folding or creasing thereof.

While the patents discussed hereinabove include means for treating entire sheets of material, U.S. Pat. No. 2,045,498 discloses fabrics which may be formed of strips cut from a web of regenerated cellulose that may be used in the trimming of hats and shoes and in knitted fabrics. The individual strips or strands lack tinsel strength and flexibility and may be treated with reagents of the softener type to relieve the stiffness to the point where the fabric is usable in a limited field. Flat strips of desired width, which are cut from the web of regenerated cellulose, are relatively hard and inelastic and possess undesired stiffness and a low order of tinsel strength. The strips are squeezed or crushed upon themselves to provide uniformly soft and pliable strands or ribbons which have relatively great tinsel strength after they are drawn through a dye including restricted axial cylindrical boars. Before being delivered to the dye, each strip is dusted or sprayed with a lubricant such as paraffin or other wax. The treatment helps to ease the stock through the dye and also operates to reduce friction of the parts as they pass over from the flat stage to the labyrinthian or involuted stage.

Prior to U.S. Pat. No. 5,088,972 and the disclosure of the apparatus and method for folding and crimping shredded strips of sheet material as disclosed therein, U.S. Pat. Nos. 2,621,567; 2,686,466; and 2,770,302 disclosed different means for attempting to shred a paper in a form-which could be utilized as a type of packing material. In one way or another, each of these devices shred or shear paper into strips arid to provide kinks to the strips at spaced-apart points along their length to produce generally zig zag strips. While the kinks or angles are obtuse and not as firmly formed or established as those disclosed in U.S. Pat. No. 5,088,972, it is nevertheless clear that despite the less efficient and effective manner in which the strips are formed, it would be advantageous having a firm and well established zig zag form. Despite the teaching of the devices disclosed in the patents if hereinabove which include method and apparatus for generally crinkling, crumpling or folding sheet material, none of these patents regarding shredding or shearing of paper to form strips suggest the use of water or other fluid to improve the resulting product formed thereby. In fact, there would clearly be some concern that any such complicated series of overlapping shredding discs or cutting wheels could properly operate in an environment including paper which was wetened or in a moistened condition.

It should be noted that the preferred machine disclosed in U.S. Pat. No. 5,088,972 includes cutting blades which are serrated. The serrated cutting blades were intended to facilitate easy shredding of the sheet material and to assist in pulling the sheet material into the shredding device once the sheet material engages the cutting blades. However, it has been found that the use of such serrated cutting blades significantly increases the dust formed during the formation of the desired strips of material. On the other hand, the preferred cutting wheel configuration disclosed in U.S. application Ser. No. 538,181 includes smooth outer surfaces which nevertheless are capable of "gripping" and pulling the material therein for the desired cutting of the sheet material into strip form. Nevertheless, the extensive cutting of the sheet material into numerous strip means produces dust material formed of extremely small pieces of material. While it is not known if such dust of small paper material is formed during the shredding by the devices disclosed in U.S. Pat. Nos. 2,621,567; 2,686,466; and 2,770,301, it is recognized that any extensive cutting of such material could result in the formation of such dust particles.

On the other hand, it is quite possible that the formation of such dust would be greater in U.S. application Ser. No. 538,181 as compared to the other devices which used an entirely different method for providing kinks or bends in the strips formed thereby. Because of the preferred method and apparatus for forming the strip means by the restriction thereof at the outlet of the cutting section, the strip means are retained within the cutting area for a significant amount of time during which the cutting wheels rotate rapidly by the collected strip means therein. This rotation of the cutting blades clearly produces friction thereon which will wear on the newly formed cut edges of the strip means to further produce the dust particles. Obviously, the use of the serrated cutting blades in U.S. Pat. No. 5,088,972 has been found to significantly increase the undesired quantity of dust created by the means for forming the strips thereof.

A number of other patents, including U.S. Pat. Nos. 2,865,080; 2,968,857; 3,235,442; and 3,859,965 disclose means for treating various filaments or fibers with some dampening or wetting element to generally improve their characteristics.

U.S. Pat. No. 2,865,080 discloses method and apparatus for crimping and relaxing filaments. Specifically, the preferred filaments include an acrylonitrile polymer in which individual filaments are crimped by feeding them into a confined space wherein the filament mass is accumulated until sufficient push is developed to open the forced-pressure exit door. Such is commonly referred to as a "stuffer-box" crimper. The method is apparently improved by the introduction of steam into the crimper chamber since the steam is both moist and hot and tends to soften the filaments so that they crimp more readily.

U.S. Pat. No. 2,968,857 discloses high bulk filamentary material and the method for producing the same in which continuous filaments or staple fibers of organic acid esters of cellulose are formed by extrusion of solutions through orvices in a member known as a jet. Accordingly, the filaments may be provided in non-circular cross sectional configurations. To lubricate the tow of such filaments, it is passed over a roller which is dipped through a throft containing water or a water emulsion of lubricants and softening agents. After the tow is passed through a first stuffing box it is again passed through a roller configuration which contains water or other lubricant.

U.S. Pat. No. 3,235,442 discloses a crimped tow of crystallizable linear condensation polyester and to the process for forming the same. The tow is drawn by being passed through a series of feed rollers which are maintained at a given uniform peripheral speed and then around additional rollers having a uniform peripheral can still be higher than that of the feed rollers. While being advanced through the speed rollers, the tow passes through a pre-wetting vessel which contains an aqueous bath which may be at room temperature or which may be heated to a temperature in the range of 40 to 70. Additional hot liquid may be sprayed on the tow as it is moved with the tow being drawn to a length several times its original length in response to the tension imposed by the draw rolls. Eventually, the tow is advanced to a "stuffer box" for producing a collection of the tow in a generally crimped, sheet form.

U.S. Pat. No. 3,859,695 discloses a stuffer crimping system for textile strands including yarns, tows or threads. It has been found desirable to introduce into the stuffing crimper chamber a fluid under pressure, such as steam, to provide the desired temperature and pressure for heating and moisture to the strands in a chamber while having due regard for the material of which the strands are made.

Clearly, any means for improving the quality of the packing product as generally disclosed in U.S. Pat. No. 5,088,972 and U.S. application Ser. No. 538,181, which are assigned to the same assignee of the present application and are incorporated by reference herein, would be desirable. It would be advantageous to include any method or apparatus which would improve the quality of the product and simplify its formation. Additionally, it would be advantageous to employ any method or apparatus which would reduce the formation of undesired dust products which tend to be entrapped in the packing product.

SUMMARY OF THE INVENTION

It is therefore an object of the invention to provide a method of forming a packing product which has the desired characteristics of a plurality of folds in each of the strip means having angles which are a staple for providing the desired resilience and side lateral support thereby.

It is a further object to provide such a method which can be controlled to facilitate the formation of the desired packing product.

It is yet another object to provide such a method of forming the preferred packing product which will minimize the formation of undesired dust products tending to be entrapped therein.

It is still another object to provide apparatus for forming the improved packing product by the preferred method.

These and other objects of the invention are provided by a preferred method of producing an improved packing product comprising the steps of: providing a roll of paper material; longitudinally withdrawing the paper material from the roll; adding water to the paper material to form a moistened the paper material; sequentially transversely cutting the moistened paper material in a transverse direction of the moistened paper material to sequentially form sheets of the moistened paper material for being separated from a remainder of the moistened paper material; pulling each sheet of the moistened paper material in a first direction away from the remainder of the moistened paper material after the transversely cutting; cutting each sheet of the moistened paper material along the first direction into a plurality of moistened strips; advancing each moistened strip in the first direction after the cutting; restricting each moistened strip from continued advancing in the first direction; sequentially folding each moistened strip by the restricting in opposition to the advancing; and allowing ea(h moistened strip to dry to form a longitudinally compressed strip.

The preferred step of sequentially folding produces a plurality of folds of the moistened strips with adjacent folds being in opposite directions. The preferred step of sequentially folding the plurality of folds is against natural resilience of the moistened strip to produce biasing at each fold tending to separate adjacent longitudinal portions of the moistened strip which adjacent longitudinal portions are adjacent to each fold and the step of allowing each moistened strip to dry provides stability to each fold tending to establish a stable angle between the adjacent longitudinal portions. The preferred method further includes the step of collecting a plurality of moistened strips in a discharge chute extending in the first direction after the sequentially folding to cause the allowing of each moistened strip to dry within the discharge chute.

The preferred step of cutting is performed by rotating two sets of alternating, overlapping cutting discs; the step of pulling each sheet includes feeding each sheet of moistened paper material between the two sets of cutting discs; and the step of advancing each moistened strip is by the rotating of at least an outer surface of a corresponding one of the cutting discs as the outer surface moves in the first direction.

The preferred step of transversely cutting is only partially through the moistened paper material to cause each sheet to be partially attached to the remainder of the moistened paper material prior to the pulling and the step of pulling includes separating each sheet from the remainder of the moistened paper material.

The preferred method further includes the steps of longitudinally cutting the moistened paper material after the adding of water to form a plurality of longitudinal segments of the moistened paper material, redirecting each longitudinal segment of the moistened paper material to produce overlapping thereof to provide the moistened paper material with layers prior to the sequentially transversely cutting, and the sequentially transversely cutting the moistened paper material includes the sheet of moistened paper material having the layers which are respectively partially attached to the layers of the remainder of the moistened paper material.

The preferred step of adding water includes adjusting an amount of the water added to the paper material to select a moisture content of the moistened paper material. The step of adding water includes rotating a roller through a container including water and against the paper material to transfer the water from the container to the paper material and the adjusting is provided by varying a rotational speed of the roller relative to the paper material. The preferred rotating is in a direction corresponding to movement of the paper material by the roller.

The objects of the invention are provided by a preferred embodiment thereof including apparatus for producing an improved packing product including a roll of paper material and a configuration for longitudinally withdrawing the paper material from the roll. A device for adding water to the paper material is used to form moistened paper material. A transverse cutter is for at least partially cutting the moistened paper material in a transverse direction of the moistened paper material to sequentially define sheets of the moistened paper material for being separated from a remainder of the moistened paper material. A feeding device is for sequentially feeding each sheet of the moistened paper material in a first direction away from the remainder of the moistened paper material after the at least partially cutting by the transverse cutter. A cutting device is for cutting each sheet of the moistened paper material along the first direction into a plurality of moistened strips. A restricting area is for restricting each moistened strip formed by the cutting device to cause sequential folding of each moistened strip. Each moistened strip is for being dried to form a longitudinally compressed strip.

The preferred cutting device for cutting each sheet of moistened paper material into the plurality of moistened strips includes two rotating sets of alternating, overlapping cutting discs and the feeding device is for directing each sheet of the moistened paper material between the two rotating sets of cutting discs.

The preferred device for adding water includes a container of water and a roller disposed to make contact with the paper material between the roll and the transverse cutter and a drive system for rotating the roller through the water and against the paper material for transferring the water from the container to the paper material. The drive system for rotating includes controls for selectively varying a rotational speed of the roller for selectively varying an amount of the water being transferred to the paper material. The drive system preferably rotates the roller in a direction corresponding to movement of the paper material.

The preferred apparatus includes a configuration for longitudinally cutting and layering the moistened paper material disposed between the device for adding water and the transverse cutter. The configuration for longitudinally cutting and layering forms a plurality of longitudinal segments of moistened paper material, redirects the longitudinal segments to produce overlapping thereof and provides layers of the moistened paper material for each sheet and each moistened strip.

BRIEF DESCRIPTION OF THE DRAWINGS

FIG. 14 is a schematic overall view of the steps of the method of the present invention.

One should understand that the drawings are not necessarily to scale and that the elements are sometimes illustrated by graphic symbols, phantom lines, diagramatic representations and fragmentary views. In certain instances, the drawings have omitted details which are not necessary to an understanding of the present invention or which render other details difficult to perceive. For example, the schematic view of FIG. 1 includes additional framing, bracketing and adjustment means which are well known in the printing and paper art for the supply and advancement of large sheets of paper from a roll. For another example, various bearings for supporting rollers and insuring free rotation thereof have been omitted. For still another example, the representations of the strips of material shown in FIGS. 10 through 13 specifically illustrate the general configurations of only a few typical strip means from the numerous individual forms produced by the preferred method and apparatus but nevertheless represent the relative characteristics of the strip means produced by the prior art method and apparatus as compared to that produced by the preferred method and apparatus of the present invention.

DESCRIPTION OF PREFERRED EMBODIMENT

Figure 1:
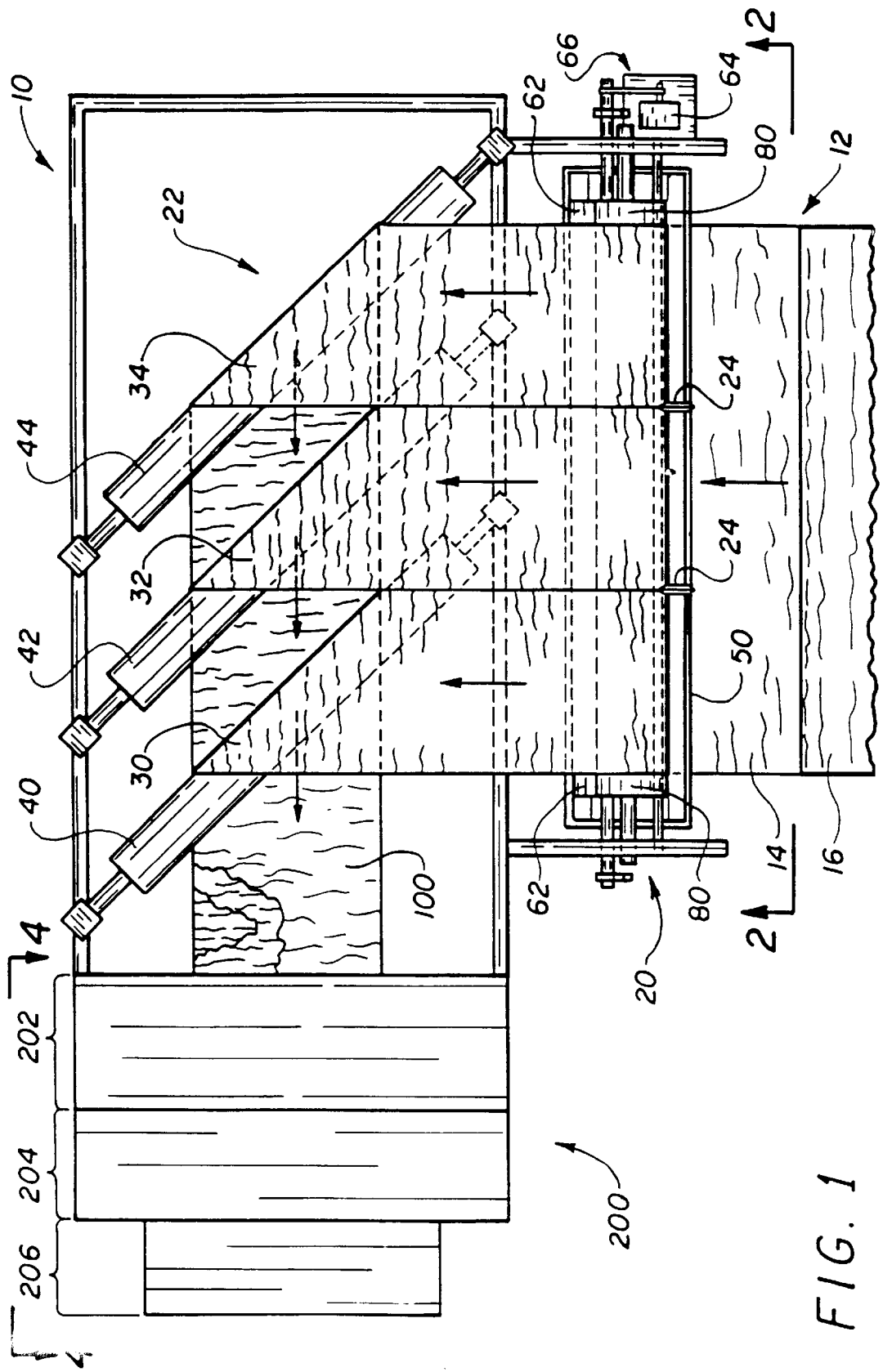
FIG. 1 is a schematic top view of the preferred method and apparatus for producing the improved packing product including various features of the invention.

As seen in FIG. 1, the preferred method and apparatus of the present invention is basically provided by a preferred packing paper apparatus 10 including a number of features which can be found in the prior art machines disclosed in U.S. Pat. No. 5,088,972 and U.S. application Ser. No. 538,181.

Basically, the preferred apparatus 10 for forming packing product includes a feed section 12 for supplying a large quantity of sheet paper 14 from a roll 16. The method of mounting and exchanging such large rolls 16 is well known in the paper art. In the preferred apparatus 10 for forming the packing product, the roll 16 includes sheet paper 14 having a transverse width of about 60 inches. The sheet paper 14, as will be seen, is slit into three separate longitudinal segments 30, 32, 34 and then redirected to provide three layers paper material 100 for advancement toward a preferred machine 200. As will be discussed hereinbelow, the machine 200 includes a feeding section 202, a cutting section 204 and a discharge section 206.

In the preferred apparatus 10, the large sheets of paper 14 are directed from the lower portion of the rolls 16 around a lower guide roller 60 through a preferred wetting or moistening system 20. From the moistening system 20, the sheet paper 14 is directed further upwardly to layering means 22 for longitudinally cutting and layering the sheet paper 14. The layering means 22 includes two longitudinal cutters 24 which basically divide the sheet paper 14 into three longitudinal segments 30, 32, 34. The longitudinal segments 30, 32, 34 are respectively reoriented about diagonal bars 40, 42, 44. The reorientation of the segments 30, 32, 34 result in a layering thereof to form combined layers of paper material 100. The paper material 100 is then directed to the machine 200 for formation of the pecking product as described hereinbelow.

As thus described, the preferred apparatus 10 includes features which are generally found in U.S. Pat. No. 5,088,972 and U.S. application Ser. No. 538,181 with the exception of the wetting or dampening system 20.

Figure 2:
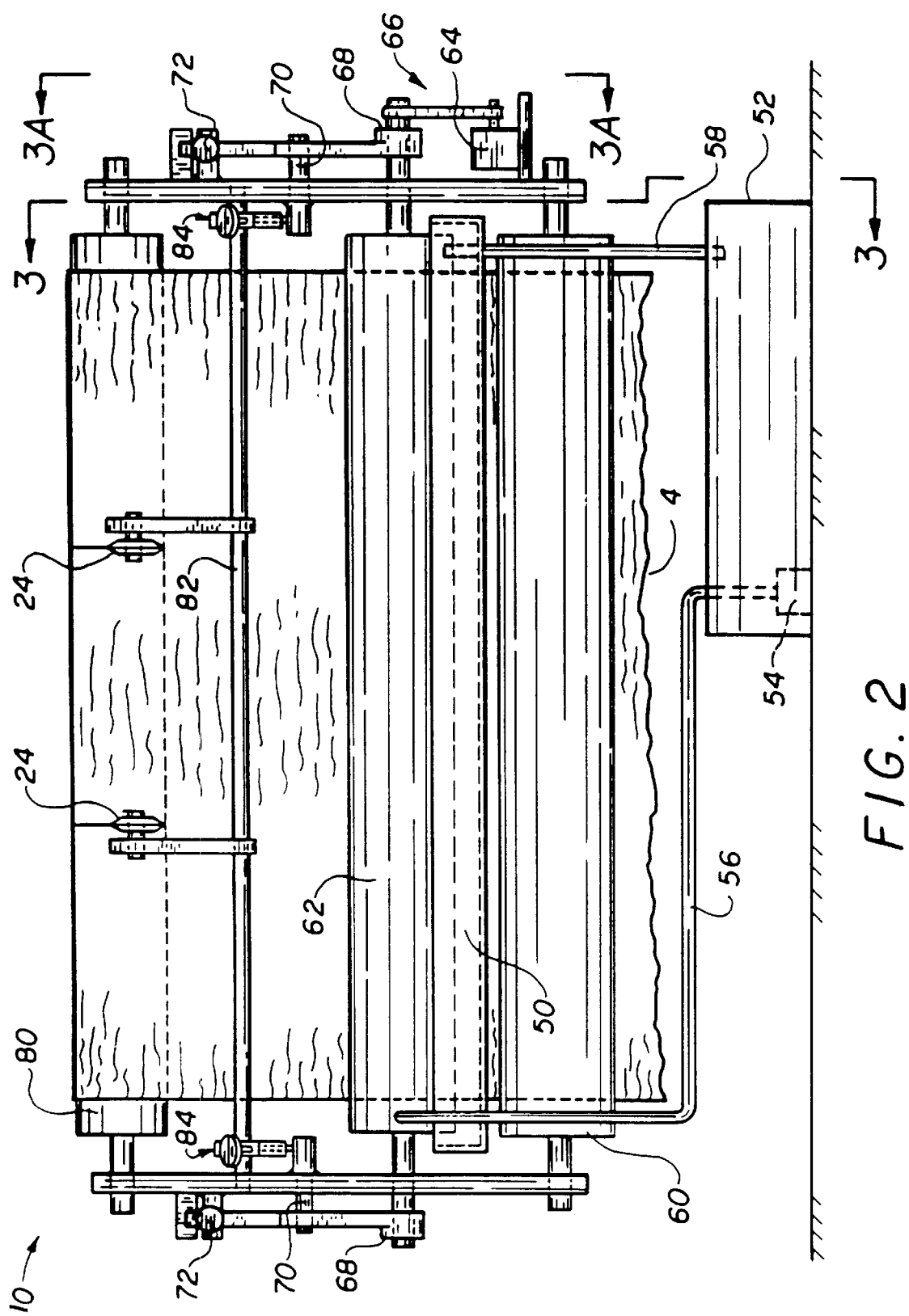
FIG. 2 is a simplified, elevational view of the apparatus shown in FIG. 1 as generally seen along Line II—II but including additional detail.
Figure 3:
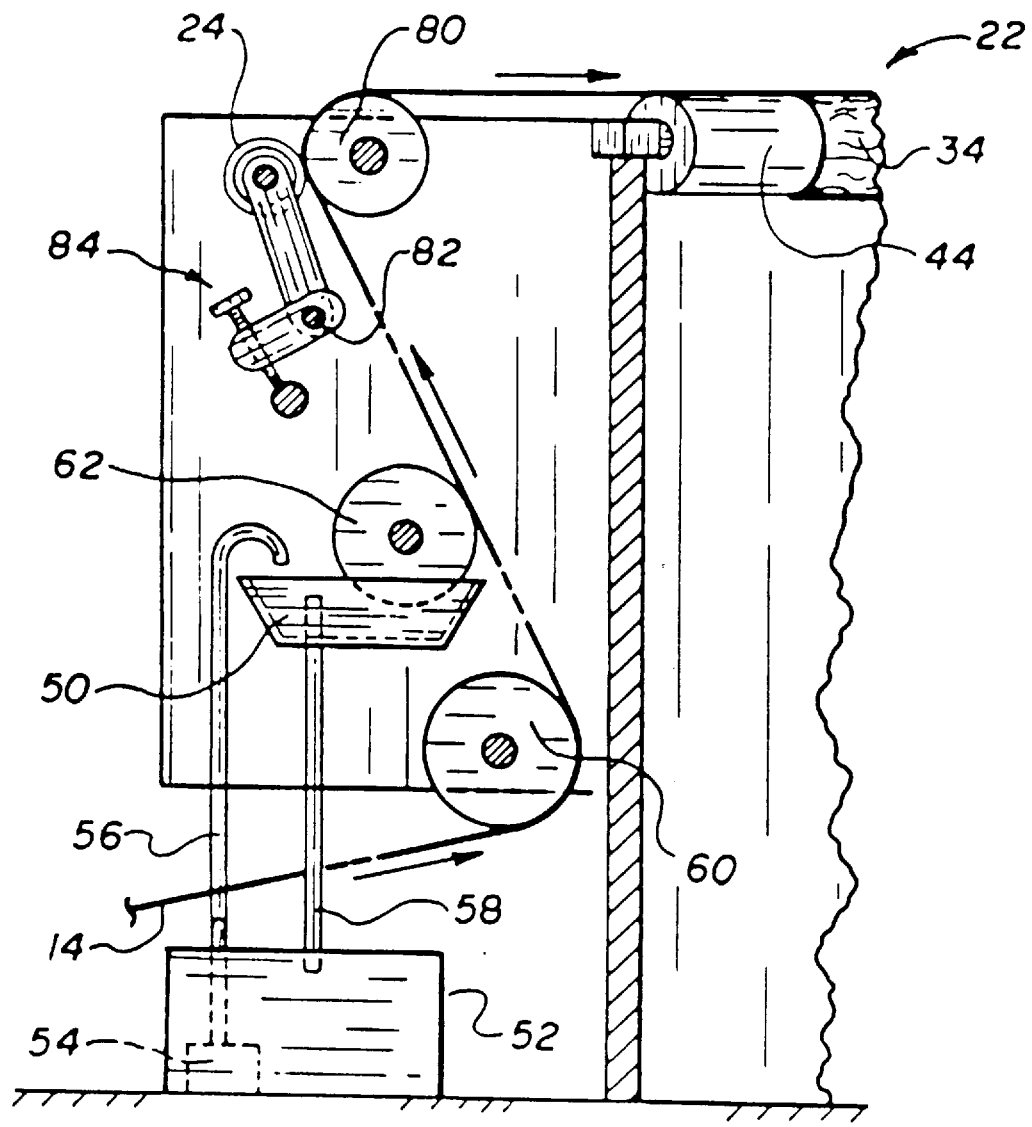
FIG. 3 is a simplified, end view of the apparatus shown in FIG. 2 including various features of the invention as seen along Line III—III in FIG. 2.

As seen in FIGS. 2 and 3, the preferred wetting or dampening system 20 includes an elongated open container 50 which extends throughout the length of the sheet paper 14 passing thereby. A continuous supply of water is provided to the container 50 from a reservoir 52 having a supply pump 54 with an associated supply line 56. The water added to the container 50 is allowed to overflow through a return line 58 at the other end thereof. Consequently, fresh water may be added to the container 50 with the excess water being returned to the reservoir 52.

To transfer the water in the container 50 to the sheet paper 14, the paper 14 is first directed around the lower guide roller 60 at the lower region of the wetting and dampening system 20. The sheet paper 14 passing from the guide roller 60 to the longitudinal cutters 24 of the layering means 22 is directed by a wetting roller 62. The wetting roller 62 is mounted to extend into the water within the container 50 and to be rotated by a motor 64 and associated drive means 66. The drive means 66 includes a drive timing pulley at the output of the motor 64 and a driven timing pulley at the end of the wetting roller 62 with a timing belt extending therebetween. The motor 64 includes means for varying the speed thereof to regulate the rotation of the wetting roll 64 in a direction indicated by the arrow with the movement of the sheet paper 14 thereby. The rotation of the wetting roller 62 causes water in the container 50 to be deposited on the cylindrical surface thereof and then transferred to the sheet paper 14 as it passes over the cylindrical surface of the wetting roller 62. The actual position of the wetting roller 62 can be adjusted through the movement of the end mounts 68 which are shown in FIG. 2 and 3 but omitted from FIG. 1. The end mounts 68 can be adjustably rotated about a pivot 70 through the positioning of an adjustment bolt 72 in opposition to biasing spring 74. As a result, the amount of water being added to the sheet paper 14 can be adjusted by two means. The increase in speed of the motor 64 would result in faster rotation of the wetting roller 62 to transfer more water to the sheet paper 14. Additionally, by the selective movement of the end mounts 68, greater pressure can be applied to the sheet paper 14 passing over the cylindrical surface of the wetting roller 62 for further insuring that water will be directed to the sheet paper 14 to increase the moisture thereof.

The moistened sheet paper 14, as seen in FIG. 3, upon passing by the wetting roller 62 is directed upwardly to the adjustable longitudinal cutters 24 for reorientation about a backing roller 80. Each of the longitudinal cutters is mounted on a rod 62 extending along the entire length of the sheet paper 14. An adjusting means 84 can be utilized to increase the pressure on each cutter 24 to insure a full longitudinal cut of the moistened sheet paper 14. Each of the longitudinal cutters 24 is aligned with a urethane surface portion (not shown) in order to provide an appropriate backing for the cutting action produced by the longitudinal cutter 24.

As a result, with the sheet paper 14 being moistened by the deposit of water thereon, each of the longitudinal segments 30, 32, 40 of paper are moistened prior to their being advanced around the diagonal bars 40, 42, 44. As the segments are rejoined for advancement to the machine 200, they form the preferred three layers of the moistened paper material 100.

As seen in FIGS. 4 through 7, the preferred embodiment of the invention includes the machine 200 for forming the preferred improved packing product which is similar to that disclosed in U.S. application Ser. No. 538,181. The preferred machine 200 has been adapted to increase the width to about 20 inches compared to that of the machine disclosed in U.S. application Ser. No. 538,181 which had a width of about 15 inches. As will be seen, other modifications to the preferred machine could be made to provide alternative configurations which are outside the scope of the present invention.

The preferred machine 200 includes the feeding section 202, the cutting section 204 and the discharge section 206. The feeding section 202 is configured to feed one or more sheets of paper material to the cutting section 204 to be longitudinally cut thereby. The strip means cut by the cutting section 204 are then discharged from the cutting section 204 to the discharge section 206 and allowed to dry.

To provide basic power to the machine 200, a feeding motor 208 is included in the feeding section 202. The feeding motor 208 has an associated reduction gear section 210 with a reduction gear output in the form of a drive sprocket 212. For powering the cutting section 204, a cutting motor 214 is provided with an associated reduction gear section 216. The output of the reduction gear section 216 is in the form of a drive sprocket 218.

Figure 9:
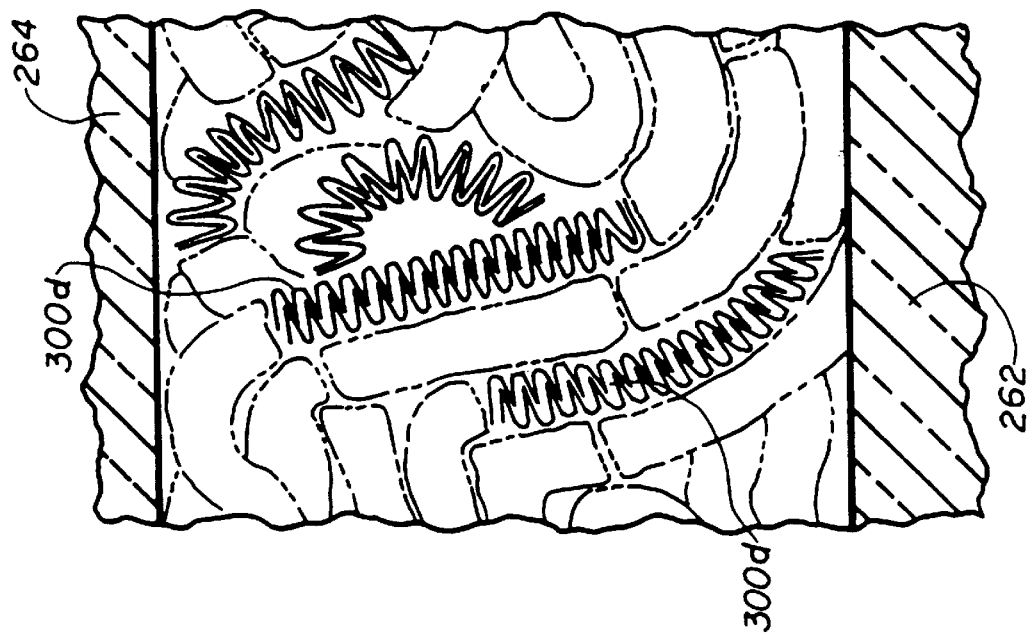
FIG. 9 is a fragmentary, sectional view as seen along Line IX—IX of FIG. 6.

To initiate the operation of the machine 200, the moistened paper material 100 for forming the preferred packing material is preferably supplied from the supply section 12 to provide one or more layers of the moistened paper material 100 to the feeding section 202. As seen in FIG. 9, the material 100 is initially directed for alignment through redirecting rollers 219. Although not specifically duplicated in FIG. 4, as discussed above, three layers of the moistened paper material 100 are preferably provided by the supply section 12.

Figure 5:
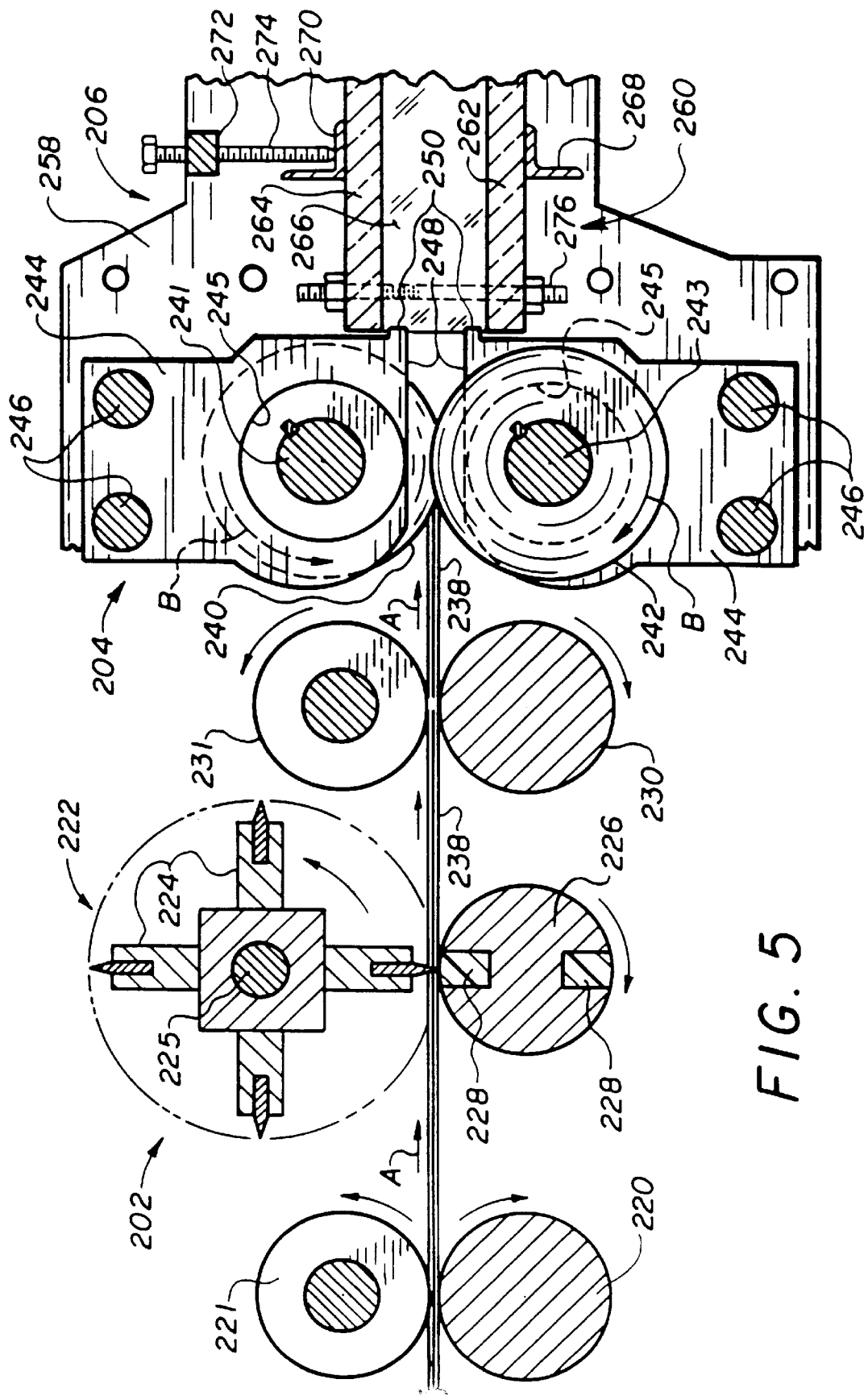
FIG. 5 is a fragmentary, sectional view of the portions of the machine shown in FIG. 4.

As seen in FIG. 5, the feeding section 202 is configured for longitudinally advancing the moistened paper material 100 in a first direction A. A first drive roller 220 feeds the moistened paper material 100 to a transverse cutting component 222. The transverse cutting component 222 includes four rotating cutting blades 224 which are mounted for rotation on a shaft 225. A back-up cylinder 226 is in alignment with the shaft 225 and includes neoprene sections 228 for specific alignment and cooperation with the blades 224.

Although not shown in the Figures, each of the preferred blades 224 includes a generally serrated edge but also includes several gaps along the lengths thereof in order to provide only a partial cut of the moistened paper material 100 as it is transferred thereunder. With the moistened paper material 100 being only partially cut to define sheets 238 which are partially attached to the remainder of the material 100, it is advanced to a second drive roller 230 for further direction to the cutting section 204. To maintain the moistened paper material 100 and sheets 238 in position for advancement to the transfer cutting component 222, a first biased roller means 221 is biased toward and in alignment with the first drive roller 220. A second biased roller means 231 is biased toward and in alignment with the second drive roller 230.

The first drive roller 220, the backing cylinder 226 and the second drive roller 230 all rotate at the same rotational speed. Each of the components in the feeding section 202 are preferably greater than 20 inches wide in order to provide the moistened paper material 100 to the cutting section 204 which, as will be seen, is also capable of accommodating paper material 20 inches wide. The first drive roller 220 is preferably knurled or rough to provide sufficient friction for advancing the moistened paper material 100 therethrough while the second drive roller 230 is preferably smooth. Additionally, the second drive roller 230 has a slightly larger diameter than the first drive roller 220 in order to keep the moistened paper material 100 tight for proper partial cutting by the transverse cutting component 222. Because of the smooth surface for roller 230, the additional tension created by the slightly larger second drive roller 230 is not sufficient to actually tear or separate the resulting sheets 238 of moistened paper material 100 from the remainder thereof simply by the action of the drive rollers 220, 230.

Figure 4:
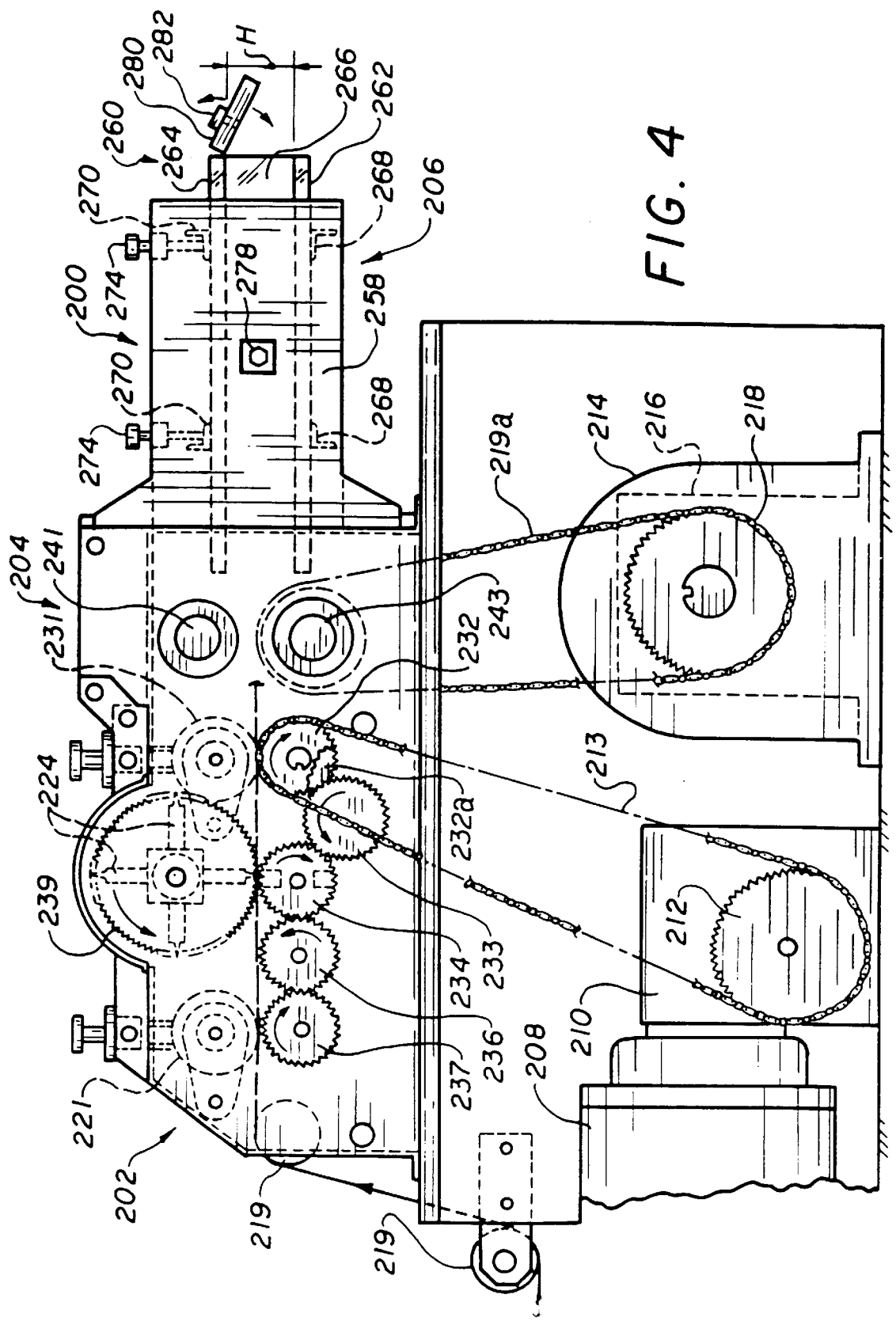
FIG. 4 is a side elevational view of the feeding and cutting sections of the machine, as seen along Line IV—IV, including additional details and various features of the invention.

The means for providing the rotation of the first drive roller 220, the cutting blade shaft 225, the backing cylinder 226, and the second drive roller 230 is shown in FIG. 4. With the basic power being provided by the feeding motor 208, the second drive roller 230 includes a driven sprocket 232 rigidly mounted on the end thereof for driving connection with a chain drive 213 from the drive sprocket 212. A gear 232a on the shaft of the second drive roller 230 is in engagement with and rotates a first idler gear 233 mounted on the side housing of the feeding section 202. The first idler gear 233 is in turn in engagement with a gear 234 associated with a backing cylinder 226. The gear 234 is in engagement with a second idler gear 236 and with a larger gear 239 connected to the rotating shaft 225 of the cutting blades 224. The gear 239 has a diameter which is twice that of the gear 234 in order to produce rotation of the shaft 225 at one half of the speed of the backing cylinder 226. Consequently, the four cutting blades 224 are brought into alignment with the two neoprene sections 228 of the backing cylinder 226 as they rotate at correspondingly different speeds. The second idler gear 236 is in engagement with and rotates the drive gear 237 on the end of the first drive roller 220. With the directional rotation of each sprocket and gear as indicated by the small arrows on FIGS. 4 and 5, it can be seen that the layers of the moistened paper material 100 will be fed towards the cutting section 204 by the feeding section 202.

In an alternative configuration, the gearing could be altered to allow the backing cylinder to have a larger diameter so that there could be included three neoprene sections thereon. The larger backing cylinder could provide greater stability throughout the width of the machine as there is being produced the desired transverse cut by the cutting blades extending transversely of the moistened paper material 328 as it advances longitudinally through the feeding section.

In the preferred machine 200, the feeding motor 208 is a variable speed motor with the reduction gear section 210 having a reduction gear ratio of ten to one. The motor 208 is preferably set to produce a feeding of the moistened paper material 100 having a width of about 20 inches at a speed of about 360 feet per minute. The spacing of the cutting blades 224 around the shaft 225 is such that the partial cut is produced every 4.4 inches along the length of the moistened paper material 100. Accordingly, the preferred sheets 238 of moistened paper material 100 to be longitudinally fed to the cutting section are 20 inches wide and 4.4 inches long.

The cutting section 204, as best seen in FIGS. 4, 5, 6 and 7, includes an upper and lower set of overlapping cutting discs 240, 242. The upper cutting discs 240 are fixedly mounted for rotation on a shaft 241 while the lower cutting discs 242 are fixedly mounted for rotation on a shaft 243. The lower shaft 243 includes a driven sprocket (not shown) and is connected by a chain 219a to the drive sprocket 218 of the cutting motor 214. The shafts 241, 243 are coupled by matching gears (not shown) for corresponding rotation in the opposite direction as generally indicated by the arrows B. The overlapping and interengagement of the discs 240, 242 are such that adjacent cutting discs 240, 242 on their respective shafts 241, 243 are separated one from the other for receipt of a cutting disc 242, 240 on the other shaft 243, 241 therebetween. The array of overlapping cutting discs 240, 242 are capable of receiving therebetween each sheet 238 of the moistened paper material 100, whether there is one or more layers, from the feeding section 202. Once directed between the cutting discs 240, 242, the sheets 238 are longitudinally cut, in the direction A, into moistened strip means with each moistened strip means including a corresponding number of layers as the original sheets 238 supplied by the feeding section 202.

The sheets 238 are generally cut to form elongated moistened strip means associated with each cutting disc 240, 242. The cuts are produced between the side edges of each cutting disc 240 and the adjacent side edges of the adjacent cutting disc 242. The moistened strip means produced by the cutting discs 240, 242 are generally maintained in alignment for passage through the cutting section 204 by an array of combers 244 associated with each set of cutting discs 240, 242.

Each comber 244 includes a central opening 245 for receipt of the corresponding shaft 241, 243 therethrough. The combers on one shaft 241, 243 are laterally or transversely aligned with corresponding cutting discs 242, 240 on the other shaft 243, 241. Each comber 244 is mounted on and supported by transverse bars 246 extending across the cutting section 204 through corresponding holes in the end of the comber 244. Despite the support by the rods 246, the preferred combers 244 are capable of limited movement along the shafts 241, 243 in the same manner as the cutting discs 240, 242.

Most significantly, each of the combers 244 includes an end face 248 in alignment with the corresponding cutting disc 240, 242 on the opposite shaft 241, 243. The configuration of cutting discs 240, 242 and aligned end faces 248 of the combers 244 produces a general region for restricted movement of the moistened strip means formed by the cutting section 204 as the sheets 238 pass therethrough. The aligned end face 248 terminates at an extension 250 of each comber 244 at the discharge side of the cutting section 204. The purpose of the extensions 250 will be discussed hereinbelow.

The cutting section 204 is powered by the motor 214 with variable speed control and includes the reduction gear 216 with a six to one reduction ratio. Each of the cutting discs 240, 242 is about ⅛ of an inch wide. Accordingly, each cutting shaft 241, 243 includes at least eighty cutting discs 240, 242 thereon to provide a total of at least one hundred and sixty cutting discs 240, 242 for the two sets to produce the desired cutting of the sheets 238 which are 20 inches wide. Preferably, the speed of the motor 214 is adjusted to provide a speed at the outer cylindrical surface of each cutting disc 240, 242 of about 380 feet per minute. In other words, tube cutting discs 240, 242 are rotating at a linear speed faster than the second drive roller 230. As a result, the faster speed of the cutting discs 240, 242 causes them to grab the sheets 238 as they enter therebetween and causes each sheet 238 to be pulled from its following adjacent sheet 238 to separate the partially cut sheets 238 for advancement through the cutting section 204. As seen in FIG. 5, the separation has not yet occurred and tends to occur as the sheet 238 is leaving the second drive roller 230. It is desirable for the drive roller 230 to maintain contact with the following adjacent sheet 238 in order to maintain the tension on the material for transverse cutting. Consequently, each sheet 238, whether having a single or multiple layer of moistened paper material 100, will be longitudinally cut into the moistened strip means in the cutting section 204 prior to the entrance or the next available sheet 238 into the cutting section 204.

It should be clear, from the discussion provided hereinabove, that the preferred machine 200 must also include some means for restricting the movement of the moistened strip means after their formation in the cutting section 204. Accordingly, the discharge section 206 is aligned with the cutting section 204 and primarily includes a discharge chute 260. The discharge chute 260 is maintained in position by framing 258 which is secured at opposite sides of the cutting section 204. The preferred discharge chute 260 is primarily formed of Plexiglas or some other durable clear plastic material The discharge chute 260 includes a lower wall 262 and an upper wall 264 with two side walls 266 therebetween. To generally support the discharge chute 260, a pair of lower brackets 268 are secured to the framing 258 to receive and support the lower wall 262 thereon. The leading end of each side wall 266 is movably secured between the lower wall 262 and the upper wall 264 by bolt means 276. To apply pressure to the lower wall 262 and the upper wall 264 for complete retention of the side walls 266 therebetween, there is provided adjustable bracketing at the top of the framing 258 for creating a downward force on the upper wall 264. Specifically, brackets 270 extend across the top surface of the upper wall 264 and are maintained in place by adjustable bolt means 274 which extend through a rigid bar 272 secured between the side framing 258. Basically, the bolt means 274 are intended, through the brackets 270, to apply reinforcing pressure to the upper wall 264 and the lower wall 262 while also providing significant frictional force on the upper and lower surfaces of the side walls 266.

Figure 6:
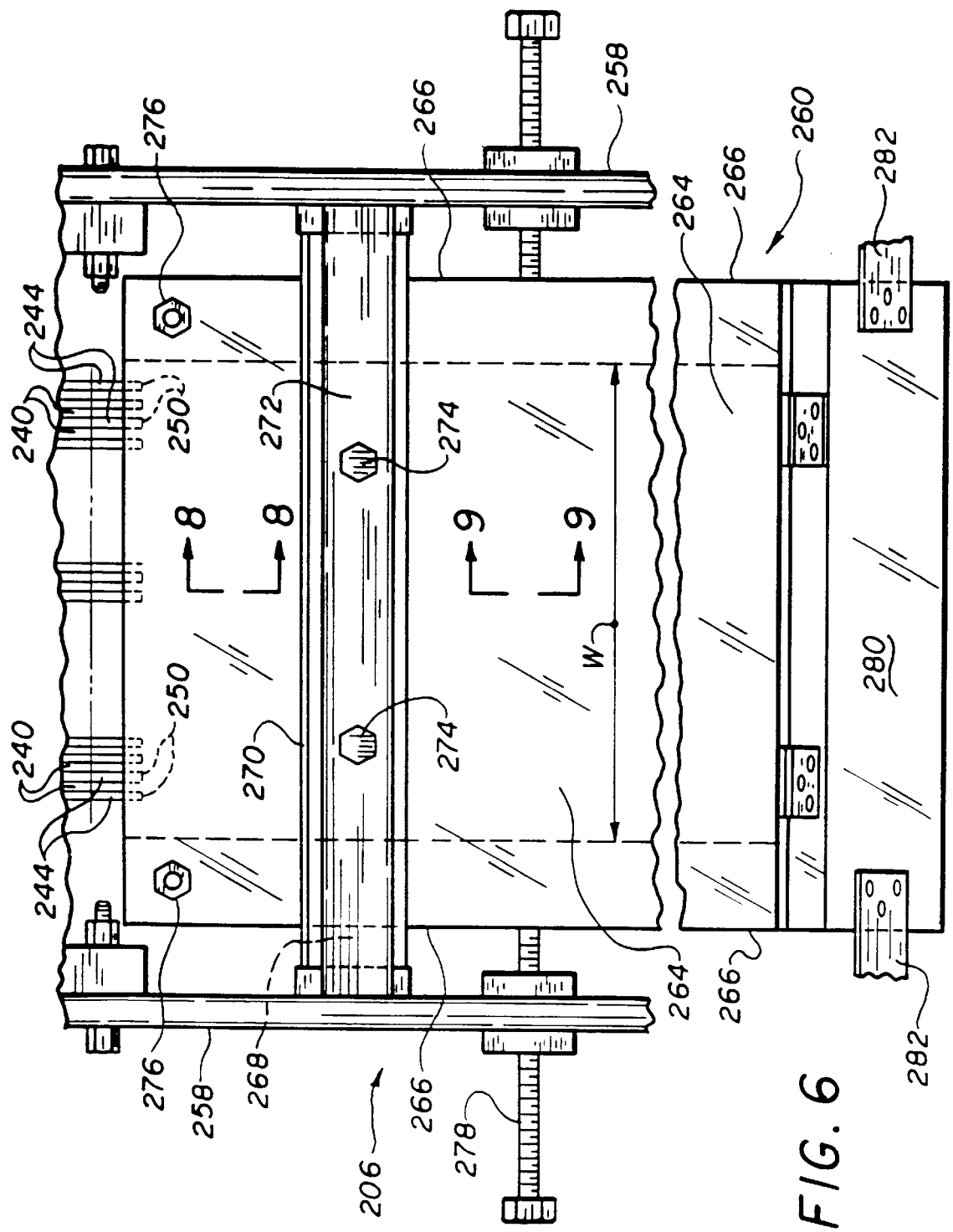
FIG. 6 fragmentary, top view of the discharge section of the portion of the machine shown in FIGS. 4 and 5.

This means of applying pressure to the side walls 266 is significant when it is understood that this preferred discharge chute 260 can be adjusted to accommodate sheets of moistened paper material having different widths as the moistened strip means formed thereby are discharged from the cutting section 204. In other words, the discharge section 206, as shown in FIG. 6, is intended to receive the strip means formed from sheets of moistened paper material which are about 20 inches wide. However, the feeding section 202 and the cutting section 204 could reasonably accommodate sheets of material as narrow as about 15 inches. The width provided in the discharge chute of the embodiment disclosed in U.S. application Ser. No. 538,181 was narrower because of the intended feeding of narrower sheets of paper material. The overall configuration is the same with the chute 260 being adapted to be wider and only modified to withstand the greater forces that may be created because of the increased volume and surface area therein.

To provide for proper discharge through the discharge section 206, this preferred chute 260 must be adjusted for producing sufficient resistance to the moistened strip means discharged from the cutting section 204. To provide for increased resistance in the discharged section 206, the mounting of the side walls 266 by the bolt means 276 allows the trailing end of each side wall 266 to be rotated to cause the discharge chute 260 to have a narrowing profile. Specifically, if the side walls 266 are to be configured with a narrower profile for the fabrication of strip means from narrower sheets of moistened paper material, the bolts 274 can be loosened to reduce the pressure between the brackets 268, 270. With the force reduced on the upper wall 264 and the lower wall 262, each side wall 266 can be rotated about its respective bolt means 276. To provide proper adjustment to the side walls 266, each frame 258 is provided with adjustable bolt means 278 for controlled positioning of the side walls 266 about the bolt means 276. Although the side walls 266 are shown to be parallel in FIG. 6, for the accommodation of sheets of moistened paper material which are about 20 inches wide, if the sheets of moistened paper material were as narrow as 15 inches, the bolts 278 could be inwardly adjusted to cause the trailing end of the discharge chute 260 to be significantly narrowed to about 15 inches. The resulting narrowing profile can create a reduced volume for the collecting of the moistened strip means therein and for providing significant restrictions on all of the moistened strip means being discharged therethrough.

Further restriction to the passage of the moistened strip means through the discharge chute 260 can be provided by the adjustable gate 280 at the output end thereof. The gate 280 is hingedly coupled to the upper wall 264. Bracketing 282 at the opposite ends of the gate 280 can be used for manual or automatic control means (not shown) for the proper positioning of the gate 280. As mentioned above, the gate 280, during continued production of the packing product of the present invention, need not always be in a closed and restricting position. In other words, once the gate 280 is closed to produce sufficient collecting of the packing product within the interior of the discharge chute 260, the general friction created by the packing product through the discharge chute 260 may be sufficient to cause adequate restrictions at the discharge of the cutting section 204 to produce the desired characteristics to the strip means as described hereinbelow.

In one configuration of the preferred machine, the discharge chute 260 has an internal height H of about 2 inches and internal width W which can be varied between about 15 and 20 inches. Because of the significant pressure and forces which are generated within the discharge chute 260, the lower wall 262 and the upper wall 264 have a thickness of about ¾ of an inch while each of the side walls 266 have a thickness of about 1–½ inches. While the preferred length of the discharge chute is about 12 inches, the length could be selected depending on the type of material being employed to produce the preferred packing product. The height of 2 inches allows the extensions 250 of each comber 244 to be loosely positioned within the interior of the chute 260 to produce a better transition from the cutting section 204 to the discharge section 206.

While the discharge chute 260 is configured for allowing adjustment of the internal width depending on the size of the sheets of material provided thereto, it should be noted that a different, simplified configuration could be employed if the machine is intended to continuously receive sheets having the same width. For example, the entire discharge chute may be formed with rigid and firmly joined top, bottom and side walls. Additionally, the bottom wall of such a discharge chute could be inclined to slope downwardly from a middle region of the discharge chute to assist in the transition of the completed packing material as it is being discharged from the end of the discharge chute. As shown in FIGS. 4, 5 and 6, the preferred embodiment, in the form of machine 200, does not include any representation of the packing product being formed thereby. However, the enlarged fragmentary view of FIG. 7 includes a representation of what is felt to occur within the interior of the cutting section 204. It should be understood that the preferred machine 200 produces an extremely packed and tight array of moistened strip means which basically comprise the preferred packing product prior to expansion, relaxation and intermixing in the discharge chute 260 and after leaving the discharge chute 260. The plurality of tightly mixed and interconnected strip means produces the packing product in such a compacted form that actual identification of the orientation and configuration of the various moistened strip means within the cutting section 204 and discharge section 206 is quite difficult. However, the best understood representation of the packing product, as it is being formed in the machine 200, is provided in a schematic form in FIGS. 7, 8 and 9.

Generally, it should be recognized that the moistened paper material for the formation of the preferred packing product includes a natural resilience with a tendency to resist folding. Whether a material in sheet form is paper, cardboard, mylar or any other material, such material typically includes a tendency to remain in a straightened form and to resist any folds or bends thereof. This principle can be readily observed by simply taking a small sheet of paper and trying to fold it in half. If one attempts to apply pressure to the fold to impart a folded memory to the sheet material, it is not uncommon for the fold to "relax" as the two halves of the paper tend to naturally separate because of the original "memory" in the paper tending to resist the fold. The same principle can also be observed if several layers are also folded at the same time.

While this condition is apparent for dry paper, it has been found that moistened paper tends to react in the same general manner but to a different degree. In other words, if the paper is slightly moistened, less force may be required to initially apply the pressure to the fold to impart a folded memory to the moistened sheet material. Additionally, when the fold relaxes as the two halves of the papers tend to naturally separate because of the original "memory" in the paper, the separation is to a lesser degree than that produced in the dry paper. Additionally, because the separation is to a lesser degree, the fold tends to be more stable and, as the paper dries, tends to retain a smaller angle at the fold than would be accomplished over the same period of time at a fold formed in the drier sheet material.

While the present invention includes means for providing water to the paper material to provide moisture thereto, it should be recalled that the natural humidity at the production site could include some moisture in the air and thus in the paper material. Consequently, the general humidity at the facility could result in a packing product having preferred characteristics, or on the other hand, could result in a detrimental situation with the packing product having less desired characteristics. While it should be clear that the adjustment of the gate 280 could affect the formation and characteristics of the folds in the strip means produced by the preferred machine, clearly, the inclusion of moistened paper material will enable the desired characteristics to be more simply and readily produced. Further, the inclusion of means for adjusting the amount of moisture within the paper material will allow convenient and reliable reproduction of the desired paper packing product in different facilities even though the different facilities may have different humidity conditions therein.

Throughout the remainder of the description provided hereinbelow, it should be noted that each of the folds produced in the preferred strip means are, at least initially, quite tight so that the adjacent longitudinal portions of the moistened strip means tend to lie in close contact. However, as will be seen, as pressure on each of the strip means is relaxed, the folds will have a natural tendency to expand or relax to cause the portions adjacent to folds to angularly separate.

Figure 7:
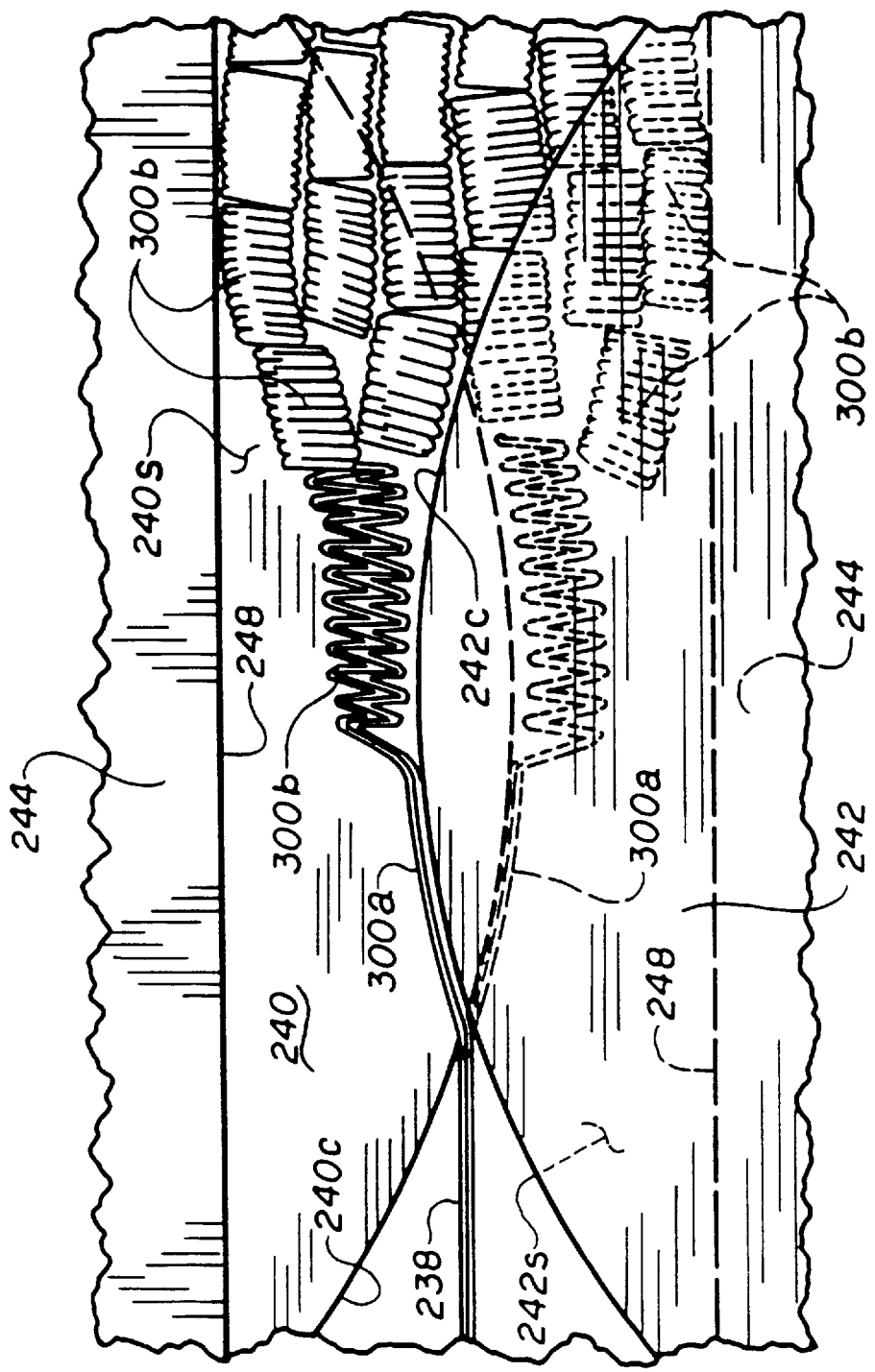
FIG. 7 is an enlarged, fragmentary view of the cutting area of the machine shown in FIGS. 4, 5 and 6.

As seen in FIG. 7, the moistened sheets 238, as they advance between the cutting wheels 240, 242, are initially cut at the side edges thereof to form initial moistened strip means 300a which tend to lie along the smooth, outer cylindrical surface 240c, 242c of the respective cutting wheels 240, 242. The initial moistened strip means 300a is constantly being advanced, at least partially, by the rotating surface 240c, 242c toward the discharge side of the cutting section 204.

However, significant resistance to each of the initially formed moistened strip means 300a is provided by a collection of previous formed moistened strip means in the discharge section 206 which will be discussed hereinbelow. It is sufficient initially to understand that a plurality of previously formed strip means are tightly collected at the discharge side of the cutting section 204. Consequently, as each initially formed moistened strip means 300a is advanced through the cutting section 204 by each of the cutting discs 240, 242 applying frictional force thereto, the resistance at the end thereof causes the initially formed moistened strip means 300a to be sequentially folded to provide a longitudinally compressed strip means 300b. The longitudinally compressed strip means 300b is formed inherently within the cutting section 204 by previously formed and fully longitudinally compressed strip means 300b collecting at the discharge side thereof.

It is impossible to stop the machine 200 and examine the area adjacent the cutting discs 240, 242, to see the exact location of the fully longitudinally compressed strip means between the cutting discs 240, 242 and the combers 244. However, it is expected that they will tend to collect to the discharge side of a connecting line between the centers of the shafts 241, 243. As a result, it is possible that the initially formed moistened strip means 300a will be relatively shorter than shown in FIG. 7. The sequential folding of each moistened strip means may begin as each moistened strip means is being longitudinally cut. However, with all the cutting discs 240, 242 rotating toward the discharge side, it would appear that the frictional force created on each fully longitudinally compressed strip means 300b would tend to cause them to collect toward the discharge side of the cutting section 204 rather than toward the connecting line of the cutting section 204.

The moving collection of fully longitudinally compressed strip means 300b is maintained in position for discharge by the aligned end faces 248 of each of the combers 244 and the extensions 250. As indicated above, the view shown in FIG. 7 represents the best understanding of the type of collection of the fully longitudinally compressed strip means 300b within the cutting section 204 at the discharge side thereof. While the outer cylindrical surface 240c, 242c does impart some compressive force on each of the initial strip means 300a as the fully longitudinally compressed strip means 300b are being formed, it should also be understood that the side surfaces 240s and 242s of each cutting wheel 240, 242 also apply side frictional forces to each of the fully longitudinally compressed strip means 300b during and after its formation.

It should be noted that the preferred machine 200 differs from the embodiment disclosed in U.S. Pat. No. 5,088,972 by the inclusion of the smooth cylindrical outer surfaces 240c and 242c of the cutting discs 240 and 242. The cutting discs of U.S. Pat. No. 5,088,972 included the serrated or tooth configuration which could grip material provided thereto and could tend to insure proper longitudinal cutting of the material for the formation of strip means. However, it has been found that one feature of the device disclosed in U.S. Pat. No. 5,088,972 was improved by the inclusion of the smooth outer cylindrical surfaces 240c, 242c because of the type of longitudinal compacting of the various strip means which occurs within the cutting section 204 of the machine 200. The smooth outer cylindrical surfaces 240c, 242c do not tend the tearing and wearing away of the material and significantly reduce the possibility of dust and other fine particles being produced. Further, as seen in FIG. 7, with the tight collection of the fully longitudinally compressed strip means 300b at the outlet side of the cutting discs 240, 242, the smooth edges of the outer surface of the cutting discs can rotate by the previously collected fully longitudinally compressed strip means 300b without excessive side ripping or tearing thereof which would clearly produce an extensive amount of dust particles.

It should now be clear that the general forces provided, by the rotation of the cutting discs 240, 242, to create the fully longitudinally compressed strip means 300b also continues to impart force to each previously formed moistened strip means to cause migration and movement in a direction toward the discharge section 206. Depending on the thickness of the material and the number of folds produced, it would not be uncommon for the fully longitudinally compressed strip means 300b, formed of 4.4 inch moistened strip means, to be only about ½ inch to about 1 inch long in the cutting sections 204.

From the description provided hereinabove, it should be clear that until the present invention, one would not be able to accurately determine what could occur inside such a shredding or cutting machine by the insertion of moistened paper material therein. One might expect that any large quantity of such paper in a moistened condition could be detrimental to the cutting discs and might even prevent effective cutting thereby. To the contrary, with the present invention, it has been found that the sheets of moistened paper material can be effectively cut by the cutting discs and generally advanced thereby for the formation of the desired longitudinally compressed strip means. Additionally, while there will always be experienced some dust particles by the general extensive cutting process for the formation of strip means by the preferred cutting section 201 or any other type of shredding machine in the prior art, the inclusion of moistened paper material has been found to generally reduce the amount of dust particles which are produced. Generally, it is felt that the additional moisture in the paper material tends to provide some lubrication during the cutting of the edges thereof and against further wear as the surfaces of adjacent cutting discs advance by the strip means.

Figure 8:
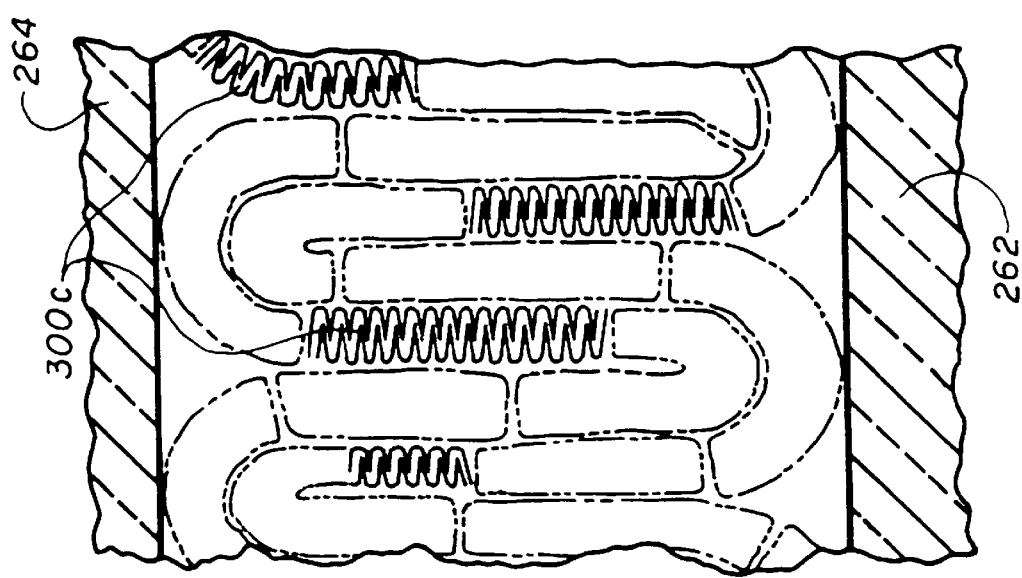
FIG. 8 is a fragmentary, sectional view as seen along Line VIII—VIII of FIG. 6.

As seen in FIG. 8, the moistened strip means, according to the best observation possible, appear to collect in some type of wave form near the entrance end of the discharge chute 260 as tightly longitudinally compressed strip means 300c advance through the discharge chute 260. While the tightly longitudinally compressed strip means 300c have very tight folds therein, it is not expected that their folds will be quite as tight as those of the fully longitudinally compressed strip means 300b as initially formed within the cutting section 204. Clearly, the resistance produced in the discharge chute 260 tending to cause the sequential folding of each of the initial moistened strip means 300a will be greater within the cutting section 204 than at subsequent positions along the discharge chute 260. The restricting force is greater at the discharge side of the cutting section 206 than at further locations along the discharge chute 260 because of the added effects of the frictional resistance of the various strip means as they tend to slide along the internal surface of the discharge chute 260. Accordingly, FIG. 8 is only a schematic representation of what appears to be occurring at the inlet end of the discharge chute 260 and the waves are probably not as uniform or as evenly positioned. However, the strip means 300c should still be quite tightly longitudinally compressed but not to the same extent as the fully longitudinally compressed strip means 300b. This tendency to be less longitudinally compressed is fully consistent with the resilient nature of the material used to form the strip means which comprises the basic packing product.

This representation in FIGS. 7 and 8 of the fully longitudinally compressed strip means 300b and the tightly longitudinally compressed strip means 300c would be similar whether the strip means are dry or moist. Without being able to accurately inspect the interior of the inlet to the discharge chute 260, a similar schematic representation of the strip means whether dry or moist would be expected. Additionally, it should be noted that the same problems concerning an accurate inspection of the interior of the cutting section 204 and the inlet to the discharge chute 260 would prevent an accurate determination of when the moistened strip means will begin to fully dry. It is expected that the moistened strip means will remain moistened for some time within the discharge chute 260 and will be significantly drier by the time the longitudinally compressed strip means discharged from the end thereof. In fact, while during the initial cutting of the sheets 238 of moistened paper material 100 the material will remain moistened to reduce the formation of dust and nevertheless to have an effective longitudinal cutting thereof for the formation of the plurality of strip means, the actual compression of each of the strip means by the cutting discs 240, 242 could clearly begin to reduce the moisture in each of the strip means and begin the drying process. Clearly, there is considerable friction created within the interior of the discharge chute and at the side and cylindrical edges of each of the cutting discs 240, 242. Accordingly, with the friction created at the discharge of the cutting section 204 and within the discharge chute 260, the drying process for each of the strip means will occur during the movement thereof through the discharge chute 260.

While, as discussed hereinabove, the moistened paper material is believed to he in a condition for the formation of less of the undesired dust material, it should also be noted that the moistened condition of the paper material might allow small edge particles thereof to be reconstituted or joined with the remainder of the strip means as such strip means tends to dry. Consequently, the moistened strip means should result in less dust particles being formed and in less dust particles being entrapped within the packing material as the individual compressed strip means begin to dry and migrate toward the exit of the discharge chute 260.

As seen in FIG. 9, at a location within the discharge chute 260 which is more remote from the cutting section 204, there is included a mixed array of less longitudinally compressed strip means 300d. Again, the less longitudinally compressed strip means 300d will further dry and include less moisture than when originally formed as strip means within the cutting section 204. As the pressure on the less longitudinally compressed strip means 300d tends to reduce, because of the opening at the discharge end of the discharge chute 260, the natural resilience of each strip means tends to cause them to expand and to be relatively repositioned within the discharge chute 260. There is a significant volumetric expansion of the strip means 300d with clear intermixing and repositioning of all of the less longitudinally compressed strip means 300d as they are approaching the end of the discharge chute 260.

With the description provided for FIGS. 7, 8 and 9, it should be clear that the basic force required to form the longitudinally compressed strip means is produced by the rotating cutting discs 240, 242 against the resistance of the previously formed longitudinally compressed strip means tending to collect throughout the length of the discharge chute 260. The natural resilience of each longitudinally compressed strip means causes them to generally longitudinally expand as they proceed toward the end of the discharge chute 260 and, once released from the discharge chute 260 into a container (not shown), further expansion of each strip means will occur. Consequently, it should now be clear that the preferred machine 200 does not include simply a shredding machine configuration for forming a collection of strip means which is compressed to form a packing product. Instead, the preferred packing product is composed of a plurality of individually longitudinally compressed strip means which tend to expand in an interlocking and resilient manner to provide the resulting packing product with individual strip means having natural resilience, a tendency to longitudinally expand, and a tendency to resist lateral or side forces.

Figure 10:
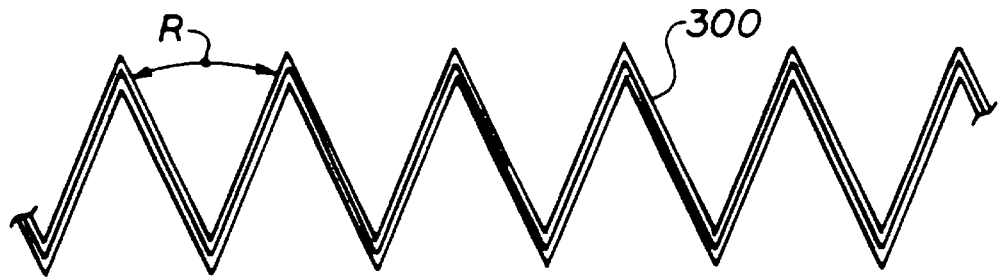
FIG. 10 is a fragmentary, side view of a representative generally compressed strip of material of the prior art at a first predetermined time after formation thereof.

Shown in FIG. 10 is a representative longitudinally compressed strip of paper material 300 of the prior art. The generally compressed strip of material 300 is not, by any means, identical to all of the strips formed by the prior art process. Obviously, other such strips would include different generally acute angles between the adjacent planar portions thereof and have such portions with different lengths. Nevertheless, the strip of paper material 300 is representative and includes typical characteristics for the purpose of comparison with a similar representative longitudinally compressed strip of material 400 which would be formed through the use of the preferred method and apparatus of the present invention. Accordingly, the strip of material 300 at a first predetermined time after being ejected from the discharge chute could include a typical angle R at the folds thereof.

Figure 11:
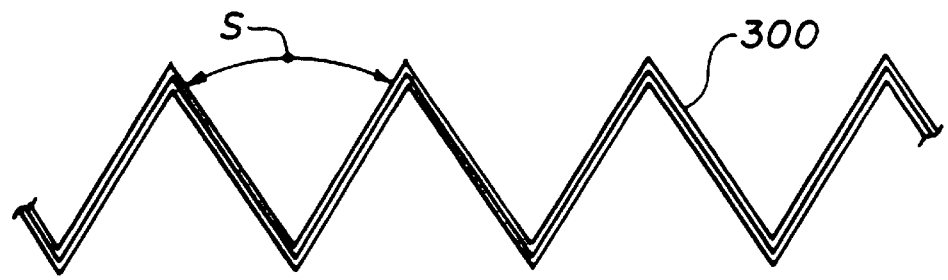
FIG. 11 is a fragmentary, side view of the same representative generally compressed strip of material of FIG. 10 after being allowed to relax for an additional predetermined amount of time.

As seen in FIG. 11, after an additional predetermined amount of time of several hours or a day or two, the same strip of material 300 would be allowed to relax to generally cause expansion thereof with a relatively larger acute angle S at the folds thereof.

Figure 12:
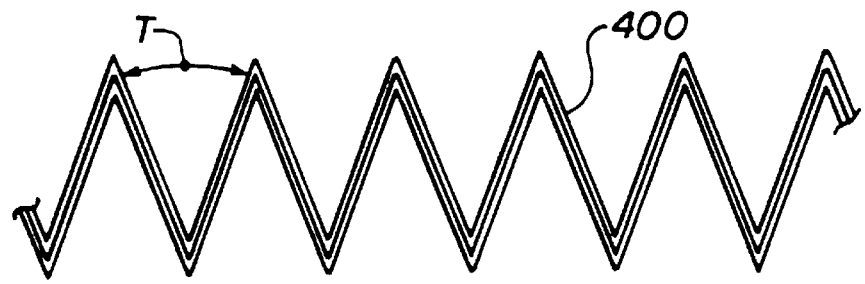
FIG. 12 is a fragmentary, side view of a preferred representative generally compressed strip of material including various features of the invention at the first predetermined time after formation thereof to demonstrate its characteristics as compared to the strip of material shown in FIG. 10.

As seen in FIG. 12, a similar preferred representative longitudinally compressed strip of material 400 is formed by the preferred method and apparatus of the present invention to have similar lengths of adjacent planar portions between the folds thereof. However, because of the introduction of moisture to the material as it is being formed, at the same predetermined time after formation as occurs with the strip of material 300 of FIG. 10, the angle T at the fold thereof would be less than the corresponding angle R of the strip of material 300. As indicated, it has been found that the introduction of moisture to the paper material will cause the resulting strip of material 400 to more readily fold and have a tendency to include smaller angles at the folds thereof.

Figure 13:
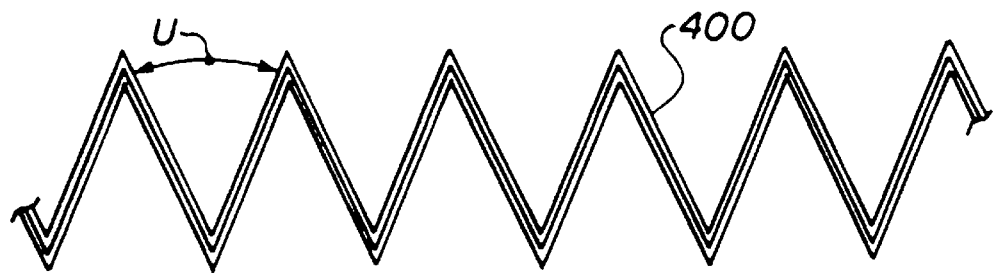
FIG. 13 is a fragmentary, side view of the preferred representative generally compressed strip of material of FIG. 12 after being allowed to relax for the same additional predetermined amount of time as occurs with the strip of material of FIG. 11 for a comparison thereof.

Further, as seen in FIG. 13, after the identical additional predetermined amount of time of several hours or a day or two, the expansion of the strip of material 400 would be such that the angle U at the folds thereof would be less than the angle S at the folds of the comparable, prior art strip of material 300 shown in FIG. 11.

It should be understood that the preferred packing product of both the prior art and the present invention include a plurality of interlocking such strips of material which continuously have a tendency to expand. Accordingly, the strips of material 300 and 400 as shown in FIGS. 11 and 13 have been basically removed from the interlocking plurality of similar strips in order to demonstrate the tendency thereof to expand when allowed to fully relax without the resistence created by being interlocked with additional such strips.

Nevertheless, it should be clear, that the use of the preferred method and apparatus of the present invention results in a more tightly formed longitudinally compressed strip of material 400 which has a tendency to maintain the angles at the folds thereof with the passage of time. The preferred method and apparatus of the present invention enables control during the formation of the longitudinally compressed strips of material independent of the moisture condition of the facility in which they are being formed to insure the quality of the strips of material as described. While there is clearly a desire to have separation between the adjacent planar portions of the strip of material at each side of the folds thereof, it is nevertheless important to insure that the acute angle at the fold is sufficiently small to maintain the tendency to longitudinally expand and the tendency to resist lateral or side forces. Obviously, if the angle at the fold is allowed to expand to an obtuse angle, the ability to expand is reduced and the ability to resist lateral or side forces would be significantly limited.

Clearly, it one were to examine each of the individual strips of material in either the prior art packing product or that formed by the preferred method and apparatus of the present invention, the individual lengths of the adjacent planar portions at each side of the various folds would be different. Nevertheless, it is felt that the representative strips of material 300 and 400 demonstrate tie relative (characteristics which can be provided to the strips of material formed by the preferred method and apparatus of the present invention.

What is claimed is:

1. An apparatus for producing a paper product from a substantially continuous web of paper, said apparatus comprising:
    a withdrawal device which longitudinally withdraws a section of the web of paper thereby forming a withdrawn section of paper;
    a moistening device which moistens the withdrawn section of paper thereby forming a moistened section of paper;
    a slitting device which cuts the moistened section of paper into strips thereby forming a plurality of moistened strips;
    a common discharge chute through which the plurality of moistened strips are advanced, said discharge chute including means for restricting the forward movement of the plurality of moistened strips in such a manner that this means along with the natural resilience of the paper alone produces substantially uniform adjacent opposite folds in each of the moistened strips thereby causing each of the strips to assume substantially the same accordion shape; and
    a drying station which allows each of the folded moistened strips to dry thereby forming a plurality of longitudinally compressed strips for use as a paper product.

2. The apparatus according to claim 1, wherein said slitting device includes two rotating sets of alternating, overlapping slitting discs and wherein said apparatus further includes a directing device which directs the moistened paper between said two rotating sets of slitting discs.

3. The apparatus according to claim 1, wherein said moistening device includes a container of water, a roller which is disposed to make contact with said withdrawn section of paper; and a rotating device which rotates said roller through said water and against the withdrawn section of paper thereby transferring said water from said container to the withdrawn section of paper.

4. The apparatus according to claim 3, wherein said rotating device includes a speed-varying device which selectively varies the rotational speed of said roller thereby selectively varying the amount of water being transferred to the withdrawn section of paper.

5. The apparatus according to claim 4, wherein said rotating device rotates said roller in a direction corresponding to the direction of withdrawal of the web of paper from the supply.

6. The apparatus according to claim 3, further including a longitudinal cutting device which is disposed between said moistening device and said slitting device and which longitudinally cuts the moistened paper whereby the moistened section of paper includes a plurality of longitudinal segments.

7. The apparatus according to claim 6, further including a redirecting/layering device which redirects and layers the longitudinal segments whereby each of the moistened strips also includes a plurality of overlapped segments.

8. The apparatus according to claim 1 further including:
    a transverse cutter which cuts a leading sheet portion of the moistened section of paper; and
    a separating device which separates the leading portion from the remaining portions of the moistened section of paper prior to the strips being folded whereby the plurality of strips are of the same unfolded length.

9. A method of producing a paper product from a substantially continuous web of paper, said method comprising the steps of:
    longitudinally withdrawing a section of the web of paper to form a withdrawn section of paper;
    moistening the withdrawn section of paper to form a moistened section of paper;
    slitting the moistened section of paper into a plurality of moistened strips;
    sequentially folding each of the moistened strips into an accordion shape to form a plurality of folded moistened strips; and
    allowing each of the folded moistened strips to dry to form a plurality of longitudinally compressed strips for use as a paper products;
    wherein said sequential folding step is accomplished only by restricting the forward advancement of the plurality of strips in a common discharge chute in such a manner that the natural resilience of the paper produces substantially uniform adjacent opposite folds thereby causing each of the strips to assume substantially the same accordion shape.

10. The method according to claim 9 wherein said allowing step further comprises the step of collecting the folded moistened strips in the discharge chute and allowing the folded moistened strips to dry within the discharge chute.

11. The method according to claim 9, wherein said slitting step includes the steps of:
    providing two sets of, alternating, overlapping slitting discs;
    pulling the moistened paper between the two sets of slitting discs; and
    advancing the moistened paper by rotating at least an outer surface of a corresponding one of the slitting discs as the outer surface moves in the advancement direction.

12. The method according to claim 11 further comprising the steps of:

transversely cutting a leading sheet portion of the moistened section of paper; and separating the leading sheet portion from the remaining portions of the moistened section of paper prior to said sequential folding step whereby said folded plurality of strips are of the same unfolded length.

13. The method according to claim 12, wherein:

the transversely cutting step comprises the step of only partially cutting through the moistened section of paper whereby the the leading sheet portion remains partially attached to the remaining portions of the moistened section of paper; and said slitting step includes separating the leading sheet portion from the remaining portions of the moistened section of paper whereby said slitting step and said separating step are performed simultaneously.

14. The method according to claim 9, further including the steps of:

longitudinally cutting the moistened section of paper whereby the moistened section comprises a plurality of longitudinal segments of moistened paper; and redirecting each of the longitudinal segments of moistened paper to produce an overlapping of the segments thereby providing the moistened section of paper with layers.

15. The method according to claim 8, wherein said moistening step includes the steps of:

selecting an amount of water to add to the withdrawn section of paper depending on the desired moisture content; and adding the selected amount of water to the withdrawn section of paper.

16. The method according to claim 15, wherein said moistening step includes the steps:

providing a container of water, and rotating a roller through the container of water and against the withdrawn section of paper to transfer water from the container to the withdrawn section of paper; and said step of selecting an amount of water includes the step of varying the rotational speed of the roller relative to the withdrawn section of paper.

17. The method according to claim 16 wherein said rotating step includes the step of rotating the roller in a direction corresponding to the movement of the withdrawn section of paper.

* * * * *

UNITED STATES PATENT AND TRADEMARK OFFICE
CERTIFICATE OF CORRECTION

PATENT NO. : 5,871,432
DATED : February 16, 1999
INVENTOR(S) : Edwin O. Beierlorzer It is certified that error appears in the above-identified patent and that said Letters Patent is hereby corrected as shown below:

<u>Title page,</u>
Item [56], References Cited, U.S. PATENT DOCUMENTS, delete reference number "2,697,887" and substitute therefore -- 2,679,887 --.

<u>Column 22,</u>
Line 45, delete "products" and substitute therefore -- product --.

<u>Column 23,</u>
Line 4, delete first occurrence of "the".

Signed and Sealed this

Twenty-second Day of June, 2004

JON W. DUDAS
*Acting Director of the United States Patent and Trademark Office*